(12) United States Patent
Boulis

(10) Patent No.: US 7,704,685 B2
(45) Date of Patent: Apr. 27, 2010

(54) IN VIVO PRODUCTION OF A CLOSTRIDIAL NEUROTOXIN LIGHT CHAIN PEPTIDE

(75) Inventor: Nicholas M. Boulis, Moreland Hills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1080 days.

(21) Appl. No.: 10/854,726

(22) Filed: May 27, 2004

(65) Prior Publication Data

US 2005/0019346 A1 Jan. 27, 2005

Related U.S. Application Data

(60) Provisional application No. 60/474,581, filed on May 30, 2003.

(51) Int. Cl.
*C12Q 1/00* (2006.01)
*C07H 21/02* (2006.01)
*C07H 21/04* (2006.01)

(52) U.S. Cl. ............................ 435/4; 536/23.7; 536/23.1

(58) Field of Classification Search .................... 514/44; 536/23.1, 23.7; 530/300, 350; 424/9.1, 9.2, 424/184.1, 234.1, 247.1
See application file for complete search history.

(56) References Cited

U.S. PATENT DOCUMENTS

| 6,139,845 | A | 10/2000 | Donovan |
| 6,214,602 | B1 * | 4/2001 | Zdanovsky .............. 435/252.3 |
| 6,306,403 | B1 | 10/2001 | Donovan |
| 2001/0053369 | A1 | 12/2001 | Donovan |
| 2002/0107199 | A1 | 8/2002 | Walker |

OTHER PUBLICATIONS

Boulis, N.M., et al. "Neuronal survival following remote adenovirus gene delivery", Journal of Neurosurgery, vol. 96, pp. 212-219, 2002.*

* cited by examiner

*Primary Examiner*—Rodney P. Swartz
(74) *Attorney, Agent, or Firm*—Kenyon & Kenyon LLP

(57) ABSTRACT

A method of producing in a cell in vivo a *clostridial* neurotoxin light chain peptide by delivering into the cell in vivo a nucleic acid construct. The nucleic acid construct comprises (a) a nucleic acid encoding a *clostridial* neurotoxin light chain peptide and (b) a regulatory sequence operably linked to the nucleic acid to allow expression of the nucleic acid. The expression of the nucleic acid produces the *clostridial* neurotoxin light chain peptide in the cell in vivo.

3 Claims, 23 Drawing Sheets

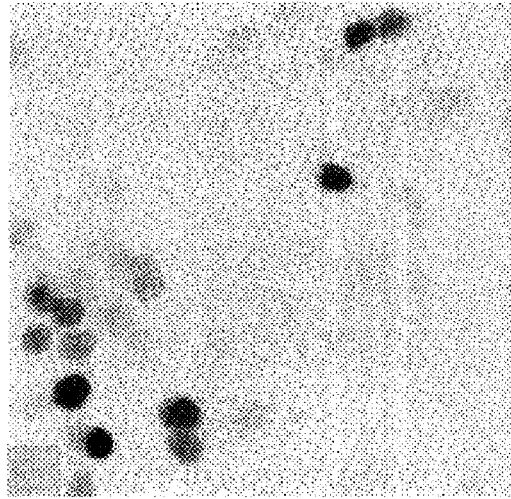

FIGURE 11A
FIGURE 11B dSC-Virus-FPS-Test 1: Baseline startle responses before fear conditioning and after fear conditioning with transinfection with tetanus virus or vehicle into the dSC/DpMe.

dSC-Virus-FPS-Test 1: Locomotor activity before fear conditioning and after fear conditioning with transinfection with tetanus virus or vehicle into the dSC/DpMe.

IN VIVO PRODUCTION OF A CLOSTRIDIAL NEUROTOXIN LIGHT CHAIN PEPTIDE

CROSS-REFERENCE TO RELATED APPLICATIONS

The present application claims priority to U.S. Provisional Application No. 60/474,581, filed May 30, 2003, which is incorporated by reference herein.

FIELD OF THE INVENTION

The present invention relates to a method of producing in a cell in vivo a clostridial neurotoxin light chain peptide.

BACKGROUND OF THE INVENTION

*Clostridial* neurotoxins are neurotoxins secreted from the *Clostridium* genus of bacteria. Such neurotoxins are potent inhibitors of calcium-dependent neurotransmitter secretion in neuronal cells. They are considered to mediate this activity through a specific endoproteolytic cleavage of at least one of the soluble N-ethylmaleimide sensitive factor (NSF) attachment protein receptor (SNARE) proteins, which include VAMP (synaptobrevin, cellubrevin), syntaxin, and SNAP-25. SNARE proteins are thought to be central to the vesicle docking and membrane fusion events of neurotransmitter secretion or hormone secretion. The neuronal cell targeting of *clostridial* neurotoxins, such as tetanus neurotoxins and botulinum neurotoxins, is considered to be a receptor-mediated event following which the toxins become internalized and subsequently traffic to the appropriate intracellular compartment where they affect their protease activity.

Botulinum neurotoxin and tetanus neurotoxin are expressed as 150-kDa single polypeptides (termed dichains) containing a disulfide bond between the 50-kDa N-terminal light chain (LC) and the 100-kDa C-terminal heavy chain (HC) (FIG. 1). A post-translational cryptic cleavage generates the mature toxin structure consisting of two chains connected by a disulfide bond. The LC contains the zinc-protease catalytic domain, responsible for the toxins' intracellular enzymatic activity. The 100-kDa HC may be further proteolyzed into a 50-kDa N-terminal membrane-spanning domain ($H_n$) and a 50-kDa C-terminal receptor-binding domain ($H_c$).

The molecular mechanism of toxin intoxication of these neurotoxins appears to involve at least three steps or stages. In the first step of the process, the toxin binds to the presynaptic membrane of the target neuron through a specific interaction between the HC and a cell surface receptor. The receptor is thought to be different for each serotype of botulinum toxin and for tetanus toxin. The carboxyl end segment of the HC, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin then translocates through the endosomal membrane into the cytosol.

The last step of the mechanism of neurotoxin activity appears to involve reduction of the disulfide bond joining the HC and LC. The entire toxic activity of botulinum and tetanus toxins is contained in the LC of the holotoxin. The LC is a zinc ($Zn^{2+}$) protease, which then selectively cleaves specific sites of one of the three SNARE proteins. Their proteolysis inhibits exocytosis and blocks acetylcholine secretion, leading ultimately to muscular paralysis. The LC itself is non-toxic because it cannot translocate through cholinergic nerve endings into cytosol.

Botulinum neurotoxins have been used in clinical settings for the treatment of neuromuscular disorders characterized by hyperactive skeletal muscles. Botulinum toxin type A has been approved by the U.S. Food and Drug Administration for the treatment of blepharospasm, strabismus, and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

SUMMARY OF THE INVENTION

In an embodiment, the present invention provides a method of producing in a cell in vivo a *clostridial* neurotoxin light chain peptide by delivering into a cell in vivo a nucleic acid construct comprising (a) a nucleic acid encoding a *clostridial* neurotoxin light chain peptide and (b) a regulatory sequence operably linked to the nucleic acid to allow expression of the nucleic acid. The expression of the nucleic acid produces the clostridial neurotoxin light chain peptide in the cell in vivo.

In another embodiment, the present invention provides a method of producing a *clostridial* neurotoxin light chain peptide in cells transplanted into a target site of a body. The method comprises transfecting cells in vitro with a nucleic acid construct comprising (a) a nucleic acid encoding a *clostridial* neurotoxin light chain peptide and (b) a regulatory sequence operably linked to the nucleic acid to allow expression of the nucleic acid in the transfected cells. The method further comprises selecting the transfected cells that express the nucleic acid and thereby produce the *clostridial* neurotoxin light chain peptide and transplanting into a target site of a body the selected transfected cells that produce a *clostridial* neurotoxin light chain peptide.

In another embodiment, the present invention provides a method of screening a test agent for inhibition of neurotoxic activity of a *clostridial* neurotoxin light chain peptide. The method comprises obtaining cells that include at least one SNARE protein that is cleavable by a *clostridial* neurotoxin light chain peptide and transfecting the cells in vitro with a nucleic acid construct. The nucleic acid construct comprises (1) a nucleic acid encoding a *clostridial* neurotoxin light chain peptide and (2) a regulatory sequence operably linked to the nucleic acid to allow expression of the nucleic acid in the transfected cells. The method further comprises selecting the transfected cells that express the nucleic acid and thereby produce the *clostridial* neurotoxin light chain peptide and exposing in vitro the selected transfected cells to the test agent. The method moreover comprises determining if the test agent inhibits the neurotoxic activity of the *clostridial* neurotoxin light chain.

BRIEF DESCRIPTION OF THE DRAWINGS

The present invention will become more fully understood from the detailed description given herein and the accompanying drawings which are given by way of illustration only, and thus are not limitative of the present invention, and wherein:

FIG. 3A is a photograph of fluorescent microscopy of HEK293 cells 24 hours after exposure to a control vector containing a LacZ reporter gene.

FIG. 3B is a photograph of a fluorescent microscopy of HEK 293 cells 24 hours after exposure to a vector containing a gene encoding a *clostridial* neurotoxin light chain peptide, an internal ribosomal entry site, and the green fluorescent protein (GFP) gene. The figure illustrates that the vector is causing expression of the gene encoding the *clostridial* neurotoxin light chain peptide and GFP reporter gene.

FIG. 11A is a photograph of a rat 72 hours after being injected with a vector containing a gene encoding a tetanus toxin light chain peptide. The arrow points to the rat's hindlimb.

FIG. 11B is a photograph of rat 72 hours after being injected with a vector containing a LacZ reporter gene. The arrow points to the rat's hindlimb.

DETAILED DESCRIPTION OF THE INVENTION

Figure 1:
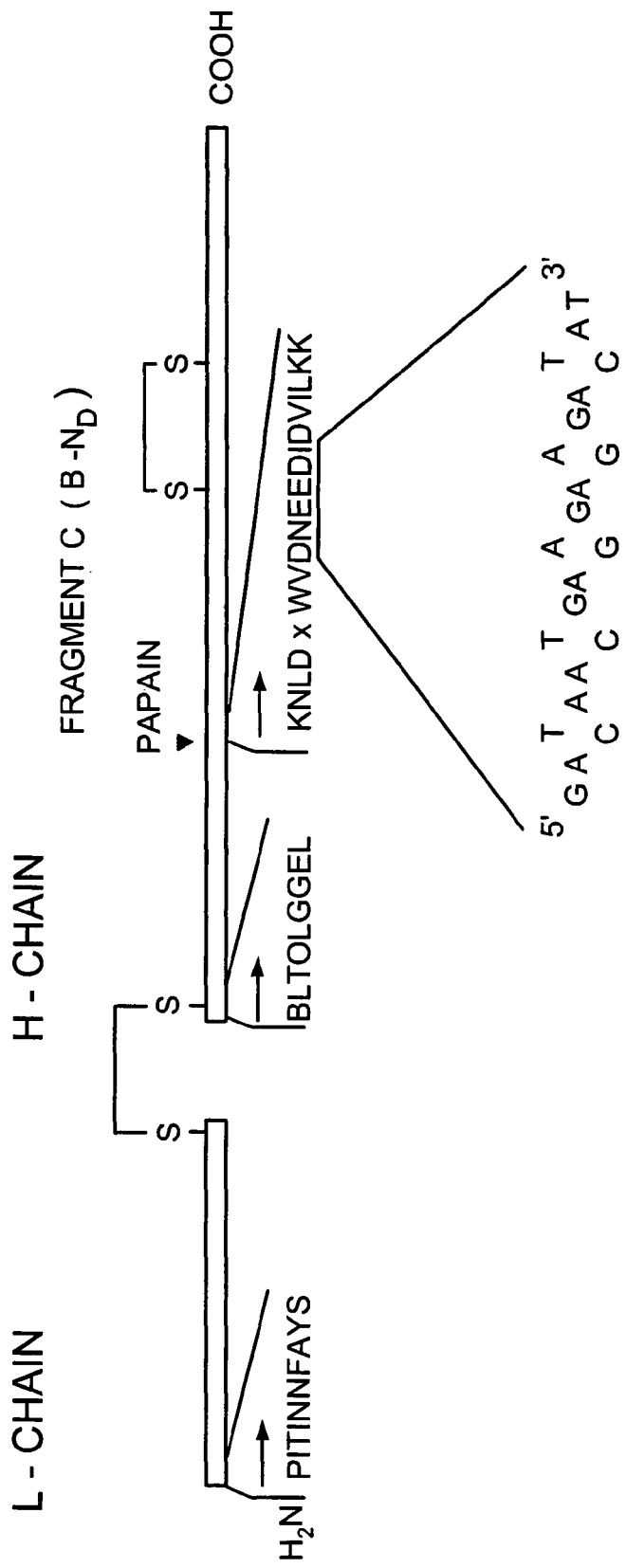
FIG. 1 is a schematic illustration of a *Clostridial* neurotoxin.

In an embodiment, the present invention provides a method of producing in a cell in vivo a *clostridial* neurotoxin light chain peptide (referred to herein as a "CNLC peptide") by delivering into a cell a nucleic acid construct comprising (a) a nucleic acid encoding a *clostridial* neurotoxin light chain peptide (referred to herein as a "CNLC nucleic acid") and (b) a regulatory sequence operably linked to the CNLC nucleic acid to allow expression of the CNLC nucleic acid (such nucleic acid construct referred to herein as a "CNLC nucleic acid construct").

As used herein, a "CNLC peptide" is a peptide having the amino acid sequence of a light chain of a *clostridial* neurotoxin secreted from any of the wild-type species of the *Clostridial* genus of bacteria (referred to herein as "a wild-type like CNLC peptide") and any functional derivative of a wild-type like CNLC peptide. The *Clostridial* genus of bacteria includes seven botulinum neurotoxins (serotypes A, B, $C_1$, D, E, F, and G) and a tetanus neurotoxin. Non-limiting examples of wild-type species from the *Clostridial* genus include *C. botulinum*, *C. tetani*, *C. argentinense*, *C. butyricum*, and *C. baratti*. As used herein, a "functional derivative of a wild-type like CNLC peptide" is any molecule that retains the function of a wild-type like CNLC peptide which permits its utility in accordance with the present invention. Such function includes inhibition of synaptic transmission and/or cleavage of any of the SNARE proteins, which include VAMP, SNAP-25, and syntaxin. The term "functional derivative" specifically includes any "fragment," "variant," or "homologue" of a wild-type like CNLC peptide. The term "fragment" refers to any peptide subset that is shorter than a wild-type like CNLC peptide. The term "variant" refers to any molecule that is substantially similar, but not identical, in structure to either a wild-type like CNLC peptide or to a fragment thereof but that still maintains the same function of a wild-type like CNLC peptide. For example, compared to the amino acid sequence of a wild-type like CNLC peptide, the variant can have one or more amino acid residues replaced (a substitution variant); one or more amino acid residues deleted (a deletion variant); or one or more amino acid residues added (an addition variant). The variant can have silent or conservative changes in amino acid residues. The term "homologue" refers to a molecule secreted from another genus of bacteria but that exhibits the same function as a wild-type like CNLC peptide.

As used herein, a "CNLC nucleic acid" is any nucleic acid having the nucleic acid sequence of a gene encoding a light chain of a *clostridial* neurotoxin secreted from any of the wild-type species of the *Clostridial* genus of bacteria (referred to herein as a "wild-type like CNLC nucleic acid") or any functional derivative of a wild-type like CNLC nucleic acid. The wild-type like CNLC nucleic acid can either be isolated from a wild-type species belonging to the *Clostridial* genus of bacteria (referred to herein as an "isolated wild-type CNLC gene") or can be a synthetic nucleic acid having the same nucleic acid sequence of an isolated wild-type CNLC gene. As used herein, an "isolated wild-type CNLC gene" is a nucleic acid molecule that is separated from other nucleic acids present in the *Clostridial* bacteria. Preferably, the "isolated" wild-type CNLC gene is free from sequences that naturally flank the nucleic acid (i.e. sequences located at the 5' and 3's of the nucleic acid) in the genomic DNA of the *Clostridial* bacteria. However, there can be some flanking nucleic acid sequences, for example, up to about 5 KB, or less, particularly contiguous peptide encoding sequences and peptide encoding sequences within the same gene but separated by introns in the genomic sequence. Essentially, an isolated wild-type CNLC gene is a nucleic acid that is isolated from remote and unimportant flanking sequences in the genomic DNA of the *Clostridial* bacteria.

A synthetic nucleic acid having the same nucleic acid sequence of an isolated wild-type CNLC gene can be constructed by recombinant DNA methods or by chemical synthesis as is well-known in the art.

As used herein, a "functional derivative of a wild-type like CNLC nucleic acid" is any nucleic acid that retains the function of encoding a CNLC peptide but does not necessarily have the same nucleic acid sequence of a wild-type like CNLC nucleic acid. The term "functional derivative" specifically includes any "fragment," "variant," or "homologue," of a wild-type like CNLC nucleic acid. The term "fragment" refers to any nucleic acid subset that is shorter than a wild-type like CNLC nucleic acid. Such fragments may be made, for example, by enzymatic digestion (e.g., using a restriction enzyme) or chemical degradation of the wild-type like CNT LC nucleic acid.

The term "variant" includes allelic variants (same locus), paralogues (different locus) and orthologues (different organism) of a wild-type like CNLC nucleic acid. The variants can contain nucleotide substitutions, deletions, inversions, and insertions of one or more nucleotides and can occur in either or both the coding or non-coding regions. The variations can produce both conservative and non-conservative amino acid substitutions. Further, the coding sequence of a functional derivative of a wild-type like CNLC nucleic acid may have a different sequence than that of a wild-type like CNLC nucleic acid, but because of the redundancy or degeneracy of the genetic code, encodes the same peptide as does the wild-type like CNLC nucleic acid. The term "homologue" includes a nucleic acid from a different genus of bacteria but that retains the function of encoding a CNLC peptide.

The CNLC nucleic acid may be in the form of RNA or DNA (including cDNA and genomic DNA). The DNA may be double-stranded or singled stranded and if single-stranded may be the coding (sense) strand or the non-coding (antisense strand).

In an embodiment, the CNLC nucleic acid of the present invention is selected from the group consisting of GenBank Accession No. AX608812, GenBank Accession No. AX608810, GenBank Accession No. AX608808, GenBank Accession No. AX608806, GenBank Accession No. AX608804, GenBank Accession No. AX608802, GenBank Accession No. AX608800, GenBank Accession No. AY166872, and GenBank Accession No. L19522.

In another embodiment, the CNLC nucleic acid according to the present invention is a nucleic acid that hybridizes under high stringency conditions to the complement of a nucleic acid selected from the group consisting of GenBank Accession No. AX608812, GenBank Accession No. AX608810, GenBank Accession No. AX608808, GenBank Accession No. AX608806, GenBank Accession No. AX608804, GenBank Accession No. AX608802, GenBank Accession No. AX608800, GenBank Accession No. AY166872, and GenBank Accession No. L19522 and that encodes a CNLC peptide. The term "high stringency conditions" refers to those conditions that are designed to permit hybridization of nucleic acids whose sequences are highly complementary to each other to thereby form a hybridization complex, and to exclude hybridization of significantly mismatched nucleic acids. Hybridization stringency is principally determined by temperature, ionic strength, and the concentration of denaturing agents such as formamide. Examples of "highly stringent conditions" for hybridization and washing may be defined as those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 .mu.g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C. (See Sambrook, Fritsch & Maniatis, Molecular Cloning: A Laboratory Manual, 2.sup.nd Ed., Cold Spring Harbor Laboratory, (Cold Spring Harbor, N.Y. 1989); Anderson et al., Nucleic Acid Hybridisation: a practical approach, Ch. 4, IRL Press Limited (Oxford, England), all of which are incorporated by reference herein. High stringency washing conditions for oligonucleotides are usually at a temperature of 0-5° C. below the thermal melting point ($T_m$) of the oligonucleotide in 6×SSC, 0.1% SDS.

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate ($NaDodSO_4$ or SDS), ficoll, Denhardt s solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: a Practical Approach, Ch. 4, IRL Press Limited (Oxford, England), which is incorporated by reference herein.

Factors affecting the stability of a hybridization complex include base composition, length, and degree of base pair mismatch. Hybridization conditions can be adjusted by one skilled in the art in order to accommodate these variables and allow nucleic acids of different sequence relatedness to form hybridization complexes. The thermal melting point ($T_m$) at which 50% of a nucleic acid hybridizes to a perfectly matched complementary nucleic acid sequence can be estimated by the following equation: The closer the hybridization and/or washing step is to the $T_m$, the higher the stringency.

$$T_m(°C) = 81.5 + 16.6(\log[Na+]) + 0.41(\% G+C) - 600/N - 0.72(\% \text{formamide})$$

where N is the length of the hybridization complex formed, [Na+] is the molar concentration of the sodium ion in the hybridization or washing solution, and % G+C is the percentage of (guanine+cytosine) bases in the hybridization complex. For imperfectly matched hybridization complexes, the melting temperature is reduced by approximately 1° C. for each 1% mismatch.

In another embodiment, a CNLC nucleic acid according to the present invention is a nucleic acid that has at least 60% sequence homology, preferably at least 70% sequence homology, more preferably at least 80% sequence homology, even more preferably 90% sequence homology and most preferably about 95% to 100% sequence homology to a nucleic acid selected from the group consisting of GenBank Accession No. AX608812, GenBank Accession No. AX608810, GenBank Accession No. AX608808, GenBank Accession No. AX608806, GenBank Accession No. AX608804, GenBank Accession No. AX608802, GenBank Accession No. AX608800, GenBank Accession No. AY166872, and GenBank Accession No. L19522 and that encodes a CNLC peptide. The percent sequence homology of a first nucleic acid to a second nucleic acid is determined by optimally aligning (with appropriate nucleotide insertions or deletions) the two nucleic acids to determined the nucleotide sequence identity of the first nucleic acid to the second nucleic acid. The term "nucleotide sequence identity" refers to exact matches between the nucleotides of two nucleic acids when their sequences are compared and the "percent sequence homology" refers to the percentage of nucleotide sequence identity of two nucleic acids.

Determining the percent sequence homology of a nucleic acid to another nucleic acid can be done by comparing the sequences with a BLASTN sequence comparison algorithm. The BLAST algorithm is commonly known in the art and is publicly accessible at the National Center for Biotechnology Information (NCBI) website (www.ncbi.nlm.nih.gov). BLASTN can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

Percent sequence homology of nucleic acids can also be determined, for example, by comparing sequence information using a GAP computer program (e.g., Needleman et al. (1970) *J. Mol. Biol.* 48:443, as revised by Smith and Waterman (1981) *Adv. Appl. Math;* 2:482), all of which are incorporated by reference herein. The GAP program defines similarity as the number of aligned nucleotides which are similar, divided by the total number of nucleotides in the shorter of the two sequences. Default parameters for the GAP program can include: (1) a unary comparison matrix (containing a value of 1 for identities and 0 for non-identities) and the weighted comparison matrix of Gribskov et al., *Nucl. Acids Res;* 14:6745 (1986), as described by Schwartz and Dayhoff, eds., ATLAS OF PROTEIN SEQUENCE AND STRUCTURE, National Biomedical Research Foundation, pp. 353-358 (1979), which is incorporated by reference herein; (2) a penalty of 3.0 for each gap and an additional 0.10 penalty for each nucleotide in each gap; and (3) no penalty for end gaps.

In another embodiment, a CNLC nucleic acid in accordance with the present invention encodes a mutated or modified heavy chain of a *clostridial* neurotoxin (in addition to encoding a light chain of a *clostridial* neurotoxin), which results in production of a *clostridial* neurotoxin peptide with a fully functioning light chain but an attenuated or incapacitated heavy chain (such that the *clostridial* neurotoxin has no capacity or reduced capacity to bind to cell membrane receptors).

A CNLC nucleic acid construct according to the present invention also comprises a regulatory sequence which is operably linked to a CNLC nucleic acid to allow expression of the CNLC nucleic acid. The term "regulatory sequence" refers to a nucleic acid sequence(s) that is required for expression of a nucleic acid to which the regulatory sequence is operably linked. By "operably linked" is meant that a nucleic acid is linked to the regulatory sequence in a manner that allows for expression of the nucleic acid. Such a regulatory sequence includes, without limitation, a promoter sequence, an enhancer sequence, a terminator sequence, a polyadenylation sequence, a splice donor sequence, a splice acceptor sequence, or any combination thereof. The regulatory sequence can direct constitutive expression of the nucleic acid to which it is operably linked in many types of host cells or can direct expression only in certain type of host cells (e.g. tissue-specific regulatory sequences). The tissue-specific regulatory sequence can include an inducible and/or repressible promoter to control expression of the nucleic acid to which it is operably linked. Non-limiting examples of suitable promoters according to the present invention include rous sarcoma virus (RSV) promoters and cytomegalovirus (CMV) promoters. Cell-specific promoters include neuron-specific enolase (NSE) and glial fibrillary acid protein (GFAP) promoters. Inducible promoters include the "Tet-on" system, and repressible promoters include the "Tet-off" system. Other suitable promoters will be readily known to one of skill in the art.

CNLC nucleic acid construct according to the present invention can be delivered into a cell by a variety of mechanisms well known in the art. Such delivery mechanisms include, without limitation, electroporation, DEAE Dextram transfection, calcium phosphate transfection, cationic liposome fusion, protoplast fusion, creation of an in vivo electrical field, DNA-coated microprojectile bombardment, injection with a recombinant replication-defective virus, homologous recombination, ex vivo gene therapy, a viral vector or non-viral vector, naked DNA transfer, or any combination thereof.

Vectors into which a CNLC nucleic acid construct of the present invention may be inserted include viral vectors and non-viral vectors, such as lipid based vectors and other vectors that are capable of delivering a CNLC nucleic acid construct in accordance with the present invention to the target cell. The vector may be a targeted vector, especially a targeted vector that preferentially binds to specific populations of cells, such as neurons. Preferably, the vectors exhibit low toxicity to a target cell and induce production of therapeutically useful quantities of a CNLC peptide in a tissue-specific manner.

Presently preferred viral vectors are attenuated viral vectors such as those derived from adenovirus (Ad), adeno-associated virus (AAV), lentivirus, or herpes virus. Both human and non-human viral vectors may be used but preferably a recombinant viral vector is replication-defective in humans. Where the vector is an adenovirus, it preferably comprises a polynucleotide having a promoter operably linked to a CNLC nucleic acid and is replication-defective in humans.

With respect to Ad vectors, a preferred form of recombinant adenovirus is a "gutless, "high-capacity", or "helper-dependent" adenovirus vector. Such a vector features, for example, (1) the deletion of all or most viral-coding sequences (those sequences encoding viral proteins), (2) the viral inverted terminal repeats (ITRs), which are sequences required for viral DNA replication, (3) up to 28-32 kb of "exogenous" or "heterologous" sequences (e.g., sequences encoding a CNLC peptide), and (4) the viral DNA packaging sequence which is required for packaging of the viral genomes into infectious capsids. For specific cells, preferred variants of such recombinant adenoviral vectors contain tissue-specific (e.g., neural tissue) enhancers and promoters operably linked to a CNLC nucleic acid.

With respect to AAV vectors, use of recombinant AAV vectors is discussed in detail in Tal, J., *J. Biomed. Sci.* 7:279-291, 2000 and Monahan and Samulski, *Gene Therapy;* 7:24-30, 2000, which is incorporated by reference herein. An AAV vector can comprise a pair of AAV ITRs which flank at least one cassette containing a tissue (e.g., neural)—or cell (e.g., motor neuron)—specific promoter operably linked to a CNLC nucleic acid. The DNA sequence of the AAV vector, including the ITRs, the promoter and CNLC nucleic acid may be integrated into the target genome.

Other viral vectors that may be use in accordance with the present invention include herpes simplex virus (HSV)-based vector, preferably HSV vectors with one or more immediate early genes (IE) deleted. In some embodiments, recombinant HSV vectors can incorporate approximately 30 kb of heterologous nucleic acid. A preferred HSV vector is one that: (1) is engineered from HSV type I, (2) has its IE genes deleted, and (3) contains a tissue-specific (e.g., neural) promoter operably linked to a CNLC nucleic acid. HSV amplicon vectors may also be used in accordance with the present invention. Typically, HSV amplicon vectors are approximately 15 kb in length, and possess a viral origin of replication and packaging sequences.

Retroviruses, such as C-type retroviruses and lentiviruses, may also be used in the present invention. For example, retroviral vectors may be based on murine leukemia virus (MLV). See, e.g., Hu and Pathak, *Pharmacol. Rev.* 52:493-511, 2000 and Fong et al., *Crit. Rev. Ther. Drug Carrier Syst.* 17:1-60, 2000, all of which are incorporated by reference herein. MLV-based vectors may contain up to 8 kb of heterologous (therapeutic) DNA in place of the viral genes. The heterologous DNA may include a tissue-specific promoter and a CNLC nucleic acid. In methods of delivery to a neural tissue, it may also encode a ligand to a neural specific receptor.

Additional retroviral vectors that may be used are replication-defective lentivirus-based vectors, including human immunodeficiency (HIV)-based vectors. See, e.g., Vigna and Naldini, *J. Gene Med.* 5:308-316, 2000 and Miyoshi et al., *J. Virol.* 72:8150-8157, 1998, all of which are incorporated by reference herein. Lentiviral vectors for use in the invention may be derived from human and non-human (including SIV, FIV, and EIAV) lentiviruses. Preferred lentiviral vectors include nucleic acid sequences required for vector propagation as well as a tissue-specific promoter (e.g., neural) operably linked to a CNLC nucleic acid. The lentiviral vectors may include viral long terminal repeats (LTRs), a primer binding site, a polypurine tract, att sites, and an encapsidation site.

A lentiviral vector may be packaged into any suitable lentiviral capsid. The substitution of one particle protein with another from a different virus is referred to as "pseudotyping." The vector capsid may contain viral envelope proteins from other viruses, for example, murine leukemia virus (MLV), vesicular stomatitis virus (VSV), and rabies-G. Both VSV and rabies-G pseudotyped vectors may also be used.

One example of a pseudotyped lentiviral vector that may be used in the present invention is an equine infectious anemia virus (EIAV) based vector that is pseudotyped with a rabies-G. Use of this pseudotyped vector is described in Mazarakis, N., et al., *Human Molecular Genetics*, Vol. 10, No. 19, 2109-2121, (2001), which is incorporated by reference herein. This vector is also commercially available from Oxford Biomedica, San Diego, Calif. It will be appreciated by one skilled in the art that other lentiviral vectors and encapsulated vectors (e.g., AAV) can be pseudotyped (e.g., with rabies-G) to target the vectors to neurons (e.g., motor neurons).

Alphavirus-based vectors, such as those made from semliki forest virus (SFV) and sindbis virus (SIN), may also be used in accordance with the present invention. Use of alphaviruses is described in Lundstrom, K., *Intervirology* 43:247-257, 2000 and Perri et al., *Journal of Virology* 74:9802-9807, 2000, which is incorporated by reference herein. Alphavirus vectors typically are constructed in a format known as a replicon. A replicon may contain (1) alphavirus genetic elements required for RNA replication, and (2) a heterologous nucleic acid such as one encoding a CNLC peptide. Within an alphavirus replicon, the heterologous nucleic acid may be operably linked to a tissue-specific (e.g., neural tissue) promoter or enhancer.

Alphavirus replicons may be targeted to specific cell types (e.g., neurons) by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell. A preferred alphavirus vector or replicon is non-cytopathic.

In many of the viral vectors compatible with the present invention, more than one promoter can be included in the vector to allow more than one heterologous gene to be expressed by the vector. Further, the vector can comprise a sequence which encodes a signal peptide or other moiety which facilitates the secretion of a CNLC peptide from the target cell.

To combine advantageous properties of two viral vector systems, hybrid viral vectors may be used to deliver a CNLC nucleic acid construct to a target tissue (e.g., neural tissue). Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless," "helper-dependent" or "high-capacity" adenoviral vector. Adenovirus/AAV hybrid vectors are discussed in Lieber et al., *J. Virol.* 73:9314-9324, 1999. Retrovirus/adenovirus hybrid vectors are discussed in Zheng et al., *Nature Biotechnol.* 18:176-186, 2000, which is incorporated by reference herein. Retroviral genomes contained within an adenovirus may integrate within the target cell genome and effect stable CNLC nucleic acid expression.

In addition to viral vectors, non-viral vectors may also be used to introduce a CNLC nucleic acid construct into a target cell. A review of non-viral vectors and non-viral vector based methods of gene delivery is provided in Nishikawa and Huang, *Human Gene Ther.* 12:861-870, 2001, which is incorporated by reference herein. One example of a non-viral vector according to the invention employs plasmid DNA to introduce a nucleic acid into a cell. Plasmid-based gene delivery methods are generally known in the art.

Synthetic gene transfer molecules may be designed to form multimolecular aggregates with plasmid DNA (e.g., harboring a CNLC nucleic acid operably linked to a neuron-specific promoter). These aggregates can be designed to bind to a target cell, such as a neuron.

Cationic amphiphiles, including lipopolyamines and cationic lipids, may be used to provide receptor-independent CNLC nucleic acid transfer into target cells. In addition, preformed cationic liposomes or cationic lipids may be mixed with plasmid DNA to generate cell-transfecting complexes. Methods involving cationic lipid formulations are reviewed in Felgner et al., *Ann. N.Y. Acad. Sci.* 772:126-139, 1995 and Lasic and Templeton, *Adv. Drug Delivery Rev.* 20:221-266, 1996, all of which are incorporated by reference herein. For gene delivery, DNA may also be coupled to an amphipathic cationic peptide (Fominaya et al., *J. Gene Med.* 2:455-464, 2000), which is incorporated by reference herein.

Vectors that involve both viral and non-viral based components may be used according to the invention. For example, an Epstein Barr virus (EBV)-based plasmid for therapeutic gene delivery is described in Cui et al., *Gene Therapy* 8:1508-1513, 2001, which is incorporated by reference herein. Additionally, vectors involving a DNA/ligand/polycationic adjunct coupled to an adenovirus is described in Curiel, D. T., *Nat. Immun.* 13:141-164, 1994, which is incorporated by reference herein.

It will be appreciated by one skilled in the art that other viral and non-viral vectors and methods of using viral and non-viral vectors are known and may be used in accordance with the present invention. These other vectors and methods are described in gene therapy treatises, such as Vector Targeting for Therapeutic Gene Delivery, Wiley-Liss, Inc. Hoboken, N.J. 2002, and Viral Vectors for Gene Therapy, Method and Protocols, Humana Press, Totowa, N.J. 2003, both of which are incorporated by reference herein.

The vector (sometimes referred to as a gene delivery vehicle), which includes a CNLC nucleic acid construct may comprise a macromolecule or complex of molecules that is capable of delivering the CNLC nucleic acid construct to the target cell, either in vitro or in vivo. The vector may include other macromolecular complexes capable of mediating delivery of a CNLC nucleic acid construct to the target cell. The vector may also comprise other components or functionalities that further modulate delivery of the CNLC nucleic acid construct and/or expression of the CNLC nucleic acid, or that otherwise provide beneficial properties to the targeted cells. Such other components may include, for example, components that influence binding or targeting to cells (including components that mediate cell-type or tissue-specific binding); components that influence uptake of the vector by the cell; components that influence localization of a CNLC nucleic acid construct within the cell after uptake (such as agents mediating nuclear localization); and components that influence expression of a CNLC nucleic acid. Such components also may include markers, such as detectable and/or selectable markers (e.g., a reporter gene, such as GFP) that can be used to detect or select for cells that have taken up and are expressing a CNLC nucleic acid delivered by the vector. Such components may be provided as a natural feature of the vector (such as the use of certain viral vectors, which have components or functionalities mediating binding and uptake), or vectors may be modified to provide such functionalities.

The selectable markers may be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994, which are incorporated by reference herein). A large variety of such selectable markers are known in the art and are generally available.

Cells into which a CNLC nucleic acid construct can be delivered include, for example, neurons such as motor neurons, pyramidal cells, interneurons and projection neurons of deep brain nuclei such as the subthalamic nucleus, thalamus, striatum, nucleus accumbens, amygdala, and hippocampus, or interneurons and projection neurons of brainstem nuclei such as the spinal nucleus of the Vth cranial nerve, or preganglionic and postganglionic neurons of the autonomic nervous system. Cells into which a CNLC nucleic acid construct can also be delivered include secretory tissue such as pancreatic cells including pancreatic islet B cells, thyroid cells, or tumors of the endocrine system including pheochromocytoma adrenal tumors and pituitary tumors including growth hormone and ACTH secreting tumors. The CNLC nucleic acid construct can be delivered to a single cell or a plurality of cells.

An assortment of delivery devices can be employed to deliver the CNLC nucleic acid construct to the desired cells of the target site. For example, the delivery device can include a hollow microneedle having an opening at its distal end through which the CNLC nucleic acid construct can be injected. A delivery system can be coupled to control delivery of the CNLC nucleic acid construct via the device. The delivery system can also include a source of CNLC nucleic construct-containing solution that is in fluid communication with the needle, such as through an interconnecting conduit. The delivery device can also be catheter. The CNLC nucleic acid construct can be delivered directly into the cells in the body of an organism with such delivery devices or other delivery devices known in the art.

In another embodiment, to control the activity of transplanted cells, the present invention provides a method of producing a *clostridial* neurotoxin light chain peptide in cells transplanted into a target site of a body. The method comprises transfecting cells in vitro with a nucleic acid construct comprising (a) a nucleic acid encoding a clostridial neurotoxin light chain peptide and (b) a regulatory sequence operably linked to the nucleic acid to allow expression of the nucleic acid in the transfected cells. The cells can be originally obtained from the organism into which the CNLC nucleic acid construct is ultimately delivered or the cells can be grown from a cell line. The transfected cells that express the CNLC nucleic acid and thereby produce the CNLC peptide are selected and the selected transfected cells are transplanted into a target site of a body, by direction injection with a microneedle, for example. Such delivery results in production of the CNLC peptide by the transplanted cells and results in inhibition of release of secretory products, such as hormones or neurotransmitters, by the transplanted cells.

The in vivo expression in a cell of a CNLC nucleic acid of a CNLC nucleic acid construct according to the present invention, produces a CNLC peptide in vivo. As described in Examples 5 and 6, such production of a CNLC peptide is detected in the target sites, such as the spinal cord and brain stem, of animals that have been injected with a CNLC nucleic acid construct. With respect to the brain stem, as described in Example 6, expression of a CNLC nucleic acid inhibits a subset of neurons within the brain stem as evidenced by the diminishment of the rat acoustic startle reflex, and not spontaneous motor activity, in rats that are administered a CNLC nucleic acid construct.

In another embodiment, the present invention provides a method of inhibiting synaptic transmission in vivo. According to this method, a CNLC nucleic acid construct is delivered into a neuron in vivo and expression of the CNLC nucleic acid of the CNLC nucleic acid construct results in production of a CNLC peptide and production of the CNLC peptide results in inhibition of synaptic transmission. For example, as described further in Examples 7-9, delivery of a CNLC nucleic acid construct induces sensorimotor dysfunction in vivo through disruption of synaptic vesicle docking. Specifically, when a CNLC nucleic acid construct is injected into an animal subject's lumbar spinal cord, the animal subject develops flaccid paralysis, shows reduced performance in standard behavioral assays that measure sensorimotor function (such as a reduced Basso-Beattie-Bresnahan (BBB) score and reduced Rotarod performance) compared to control animal subjects and compared to the same animal subject's behavior prior to injection with the CNLC nucleic acid construct.

Further, as described in Example 9, administration of a CNLC nucleic acid construct and subsequent expression of a CNLC nucleic acid can inhibit synaptic transmission at the neuromuscular junction as evidenced by reduction of evoked motor responses of a gastrocnemius muscle resulting from sciatic nerve stimulation of animals to whom a CNLC nucleic acid construct is administered ("experimental animals"). Specifically, in experimental animals observed over a five day period, the same level of stimulation to the sciatic nerve evokes a robust response in the gastrocnemius muscle on the day of administration of a CNLC nucleic acid construct but fails to produce a response five days thereafter. Moreover, while no change in stimulus response threshold is detected in control animals, the threshold for evoked motor response in experimental animals triples between the day of administration of the CNLC nucleic acid construct and the fifth day thereafter. Also, the pattern of response extinction between control animals and experimental animals shows a marked difference. Specifically, the magnitude of the evoked motor response in control animals diminishes as the synapse at the neuromuscular junction is overdriven. Such an extinction pattern is absent in experimental animals at more than twice the initial stimulation level. When the evoked motor response appears, it is at a stimulation that is three times that required on day zero of observation and shows a distinctly different extinction pattern marked by profound delay in response build-up. Taken together, such evoked gastrocnemius muscle response to sciatic nerve stimulation in experimental animals demonstrates that expression of a CNLC nucleic acid in the spinal cord alters synaptic transmission at the neuromuscular junction.

Such inhibition of synaptic transmission by a CNLC nucleic acid construct is not due to motor neuron death induced by administration of a CNLC nucleic acid construct as shown by Example 10 where the effect of CNLC nucleic acid expression on motor neuron density is measured in vivo and in vitro. Specifically, after exposing motor neuron cultures to a CNLC nucleic acid construct ("experimental culture") or a control nucleic acid construct ("control culture"), there is no statistical difference in the mean percentage of motor neurons present in the experimental culture and the control culture. Rat spinal cord sections analyzed after in vivo delivery of a CNLC nucleic acid construct ("experimental spinal cord sections") or a control nucleic acid construct ("control spinal cord sections") also reveals no statistical difference in the motor neuron density between experimental spinal cord sections and control spinal cord sections.

Example 11 further illustrates that inhibition of synaptic transmission by a CNLC nucleic acid construct is not due to motor neuron death induced by administration of a CNLC nucleic acid construct as evidenced by functional recovery of animals to whom a CNLC nucleic acid construct is administered ("experimental animals"). Such experimental animals initially exhibit motor deficit as assessed by standard assays of motor function (BBB assessments and unilateral hindlimb grip strength measurements) after CNLC nucleic acid construct administration but then show significant recovery of function twenty to thirty days after administration. Thus, experimental animals depict a functional motor deficit after being injected with a CNLC nucleic acid construct and a subsequent improvement in such functional deficit after time, indicating that the functional deficit is due to CNLC nucleic acid expression and not to motor neuron death.

In another embodiment, the present invention provides a method of cleaving a SNARE protein in vivo. According to this method, a CNLC nucleic acid construct is delivered into a cell in vivo and expression of a CNLC nucleic acid of the CNLC nucleic acid construct produces a CNLC peptide that cleaves the SNARE protein. The SNARE protein can be any SNARE protein such as, for example, VAMP 1 (also known as synaptobrevin I), VAMP-2 (also known as Synaptobrevin II), VAMP-3 (also known as Cellubrevin), VAMP-5, VAMP-7 (also known as TI-VAMP), VAMP-8 (also known as endobrevin), syntaxin 1A and 1B, syntaxin 2, syntaxin 3, syntaxin 4, syntaxin 7, syntaxin 8, SNAP 23 (also known as Syndet), SNAP 24, SNAP 25A and 25B, synaptotagmin I, synaptotagmin II, synaptotagmin III, synaptotagmin V, or synaptotagmin X. For example, as described further in Example 3, when protein extracted from mouse cortex and cerebellum containing VAMP is incubated with a CNLC peptide produced by cells infected with a CNLC nucleic acid construct and western blots are performed using an antibody against VAMP, there is no discrete band at the appropriate weight for synaptobrevin, indicating cleavage of VAMP by the CNLC peptide.

In another embodiment, the present invention provides a method of reducing spasticity in a mammal. According to this method, a CNLC nucleic acid construct is delivered into a cell of a mammal and expression of a CNLC nucleic acid of the CNLC nucleic acid construct produces a CNLC peptide that reduces spasticity in the mammal. For example, as described further is Example 12, when spastic mice are injected with a CNLC nucleic acid construct, such mice exhibit reduced spasticity and gastrocnemius muscle contractures as measured on a modified Ashworth scale and as measured by the length of the gastrocnemius muscle and tibia.

In another embodiment, the present invention provides a method of reducing spasticity associated with spinal cord injury, cerebral palsy, or multiple sclerosis in a mammal. According to this method, a CNLC nucleic acid construct is delivered into a cell of a mammal and expression of a CNLC nucleic acid of the CNLC nucleic acid construct produces a CNLC peptide that reduces spasticity associated with spinal cord injury in a mammal. For example, as described further in Example 13, when rats with induced spinal cord injury are injected with a CNLC nucleic acid construct, such rats show reduced spasticity as measured by dynamic force amplitude assays and incline plane assays.

In another embodiment, the present invention provides a method of alleviating Parkinsonian symptoms such as bradykinesia and rigidity. According to this method, a CNLC nucleic acid construct is delivered into cell of a mammal and expression of a CNLC nucleic acid of the CNLC nucleic acid construct produces a CNLC peptide that alleviates the Parkinsonian symptoms. For example, as described further in Example 14, the CNLC nucleic acid construct can increase spontaneous movements and decrease rigidity and bradykinesia in Parkinsonian mammals. The cells into which the CNLC nucleic acid construct is delivered include, for example, neurons of the globus pallidus, and/or neurons of the subthalamic nucleus. In other embodiments, the present invention provides methods of alleviating the symptoms associated with other movement disorders such as tremors and dystonia. For movement disorders, the cells into which the CNLC nucleic acid construct are delivered include, for example, neurons of the globus pallidus, the subthalamic nucleus, the ventral intermediate nucleus of the thalamus, or any combination thereof. In the case of tremors, preferably the CNLC nucleic acid construct in delivered into the neurons of the ventral intermediate nucleus and in the case of dystonia, preferably the CNLC nucleic acid construct is delivered into the neurons of the globus pallidus.

In another embodiment, the present invention provides a method of reducing epileptic seizures, such as the duration and/or frequency of seizures. According to this method, a CNLC nucleic acid construct is delivered into cell of a mammal and expression of a CNLC nucleic acid of the CNLC nucleic acid construct produces a CNLC peptide that reduces the duration and/or frequency of epileptic seizures. The cells into which the CNLC nucleic acid construct is delivered include, for example, neurons of the hippocampus, cortex, such as the motor cortex, dentate gyrus, or any combination thereof. For example, as described further in Example 15, administration of a CNLC nucleic acid construct reduces seizure duration and frequency in epileptic rats.

In another embodiment, the present invention provides a method of inhibiting the secretion of hormones from endocrine cells or secretory tumors in a mammal. According to this method, a CNLC nucleic acid construct is delivered into an endocrine cell or secretory tumor of a mammal and expression of a CNLC nucleic acid of the CNLC nucleic acid construct produces a CNLC peptide that inhibits secretion of hormones from the endocrine cell or secretory tumor. Performance of such a method can be used to treat endocrine disorders related to oversecretion of hormones, such as, for example, acromegaly, adrenal gland disorders including pheochromocytoma, amyloidosis, diabetes, growth disorders, hirsutism, hyperinsulinemia, hyperparathyroidism, pituitary tumors and other endocrine tumors, Cushing's disease, or any combination thereof. Performance of such a method may also be applicable to tumors that develop secretion of active hormones including gastrinomas and Cushing's syndrome.

When using a CNLC nucleic acid construct of the present invention for neuroinhibition and/or stereotactic modulation in a patient, the patient to be treated is preferably placed in a stereotaxis frame to pinpoint the target site in the brain for injection (for a discussion of the method see Gildenberg P L, and Tasker R R. Textbook of Stereotactic and Functional Neurosurgery. McGraw Hill, N.Y., 1998). Targeted synaptic inhibition and stereotactic neuromodulation using a CNLC nucleic acid construct according to the present invention can be used for the treatment of neural disorders including movement disorders, such as spasticity, tremors, and dystonia, psychiatric disorders, such as OCD, eating disorders (e.g., morbid obesity and anorexia), pain, such as malignant pain and chronic pain, neurodegenerative disorders, such as epilepsy, Parkinson's disease, motor neuron disease, and diabetic neuropathy, traumatic disorders, such as spinal cord injury, peripheral nerve injury, vascular disorders, or any combination thereof. It will be appreciated by one skilled in the art that other neural disorders can be treated by CNLC nucleic acid constructs according to the present invention.

During targeted neuroinhibition and/or stereotactic modulation, a CNLC nucleic acid construct can be delivered to a target cell in the form of an injectable preparation containing pharmaceutically acceptable carrier, such as saline, as necessary. Other pharmaceutical carriers, formulations and dosages can also be used in accordance with the present invention When using a CNLC nucleic acid construct for neuroinhibition and/or stereotactic modulation, a CNLC peptide can be expressed within the target tissue for any suitable length of time, including transient expression and long-term expression. Preferably, the CNLC peptide is expressed in therapeutic amounts for a suitable and defined length of time.

A therapeutic amount is an amount, which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. Specific dosages of proteins, nucleic acids, or small molecules can be determined readily determined by one skilled in the art.

In another embodiment, the present invention provides a method of a screening a test agent for inhibition of the neurotoxic activity of a CNLC peptide to determine if the test agent is a potential CNLC peptide countermeasure. Such neurotoxic activity refers to the inhibition of synaptic transmission effectuated by a CNLC peptide.

Figure 24:
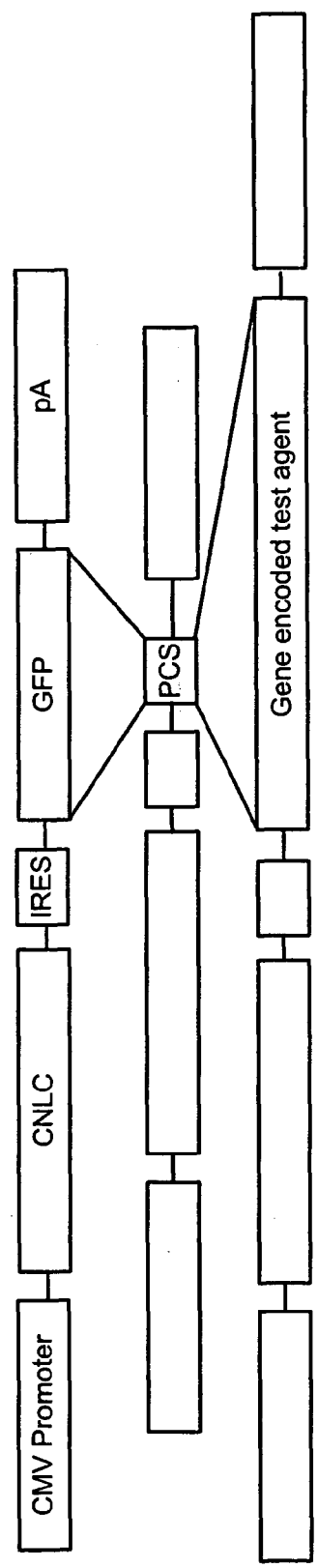
FIG. 24 is a schematic diagram illustrating the conversion of an expression cassette to contain a gene of a potential protein countermeasure.
Figure 25:
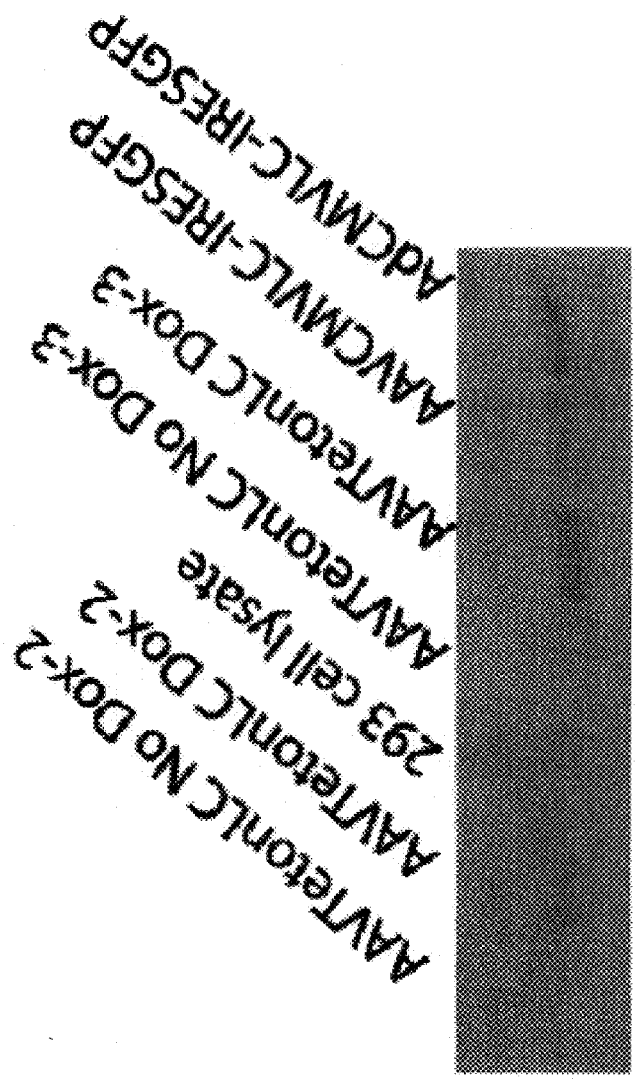
FIG. 25 is a western blot stained with an anti-LC antibody demonstrating the comparative production of LC by cells exposed to AdLC, AAVCMVLC, and AAVTet-onLC in the presence and absence of doxycycline.

According to this method, cells are obtained that include at least one SNARE protein that is cleavable by a CNLC peptide. Such cells are transfected in vitro with a nucleic acid construct. The nucleic acid construct comprises (a) a CNLC nucleic acid encoding a CNLC peptide and (b) a regulatory sequence operably linked to the CNLC nucleic acid to allow expression of the CNLC nucleic acid in the transfected cells. The transfected cells that express the CNLC nucleic acid and thereby produce the CNLC peptide are selected. The selected transfected cells are exposed in vitro to the test agent and it is determined if the test agent inhibit the neurotoxic activity of the *clostridial* neurotoxin light chain, by measuring, for example, the proteolytic breakdown of SNARE proteins. Such proteolytic breakdown can be determined using western blotting or other known diagnostic techniques.

Where the test agent is a protein, the test agent can be co-expressed with the CNLC peptide in the intracellular space of the target cells or tissue. The test agent can be co-expressed with the CNLC nucleic acid by including the gene that encodes the test agent in the CNLC nucleic acid construct along with the CNLC nucleic acid. As illustrated in FIG. 24, the structure of such a construct comprises (a) a CNLC nucleic acid and (b) a regulatory sequence operably linked to the CNLC nucleic acid to allow expression of the CNLC nucleic acid in the transfected cells, and (c) gene encoding the test agent that has potential CNLC peptide inhibitory activity (i.e. is a protein countermeasure). Co-expression of the CNLC nucleic acid and the test agent using the same nucleic acid construct may be used because the test agent protein will be co-localized with the CNLC peptide. Alternatively, the test agent and the CNLC peptide can be co-expressed using separate nucleic acid constructs.

Where the test agent and the CNLC peptide are co-expressed using the same nucleic acid construct, the test agent gene may be included in the CNLC nucleic acid construct downstream of the CNLC nucleic acid so that the test agent is expressed in the target cell at lower volume than the CNLC peptide. This strategy may be used because it models the clinical environment where the test agent delivery will more than likely occur at a lower concentration than the toxin itself. Alternatively, the test agent gene may be included in the CNLC nucleic acid construct upstream of the CNLC nucleic acid.

It will be appreciated to one skilled in the art that a CNLC nucleic acid construct according to the present invention can be used in other assays.

EXAMPLES

The present invention is further illustrated by the following specific examples. The examples are provided for illustration and are not to be construed as limiting the scope or content of the invention in any way.

Example 1

Figure 2:
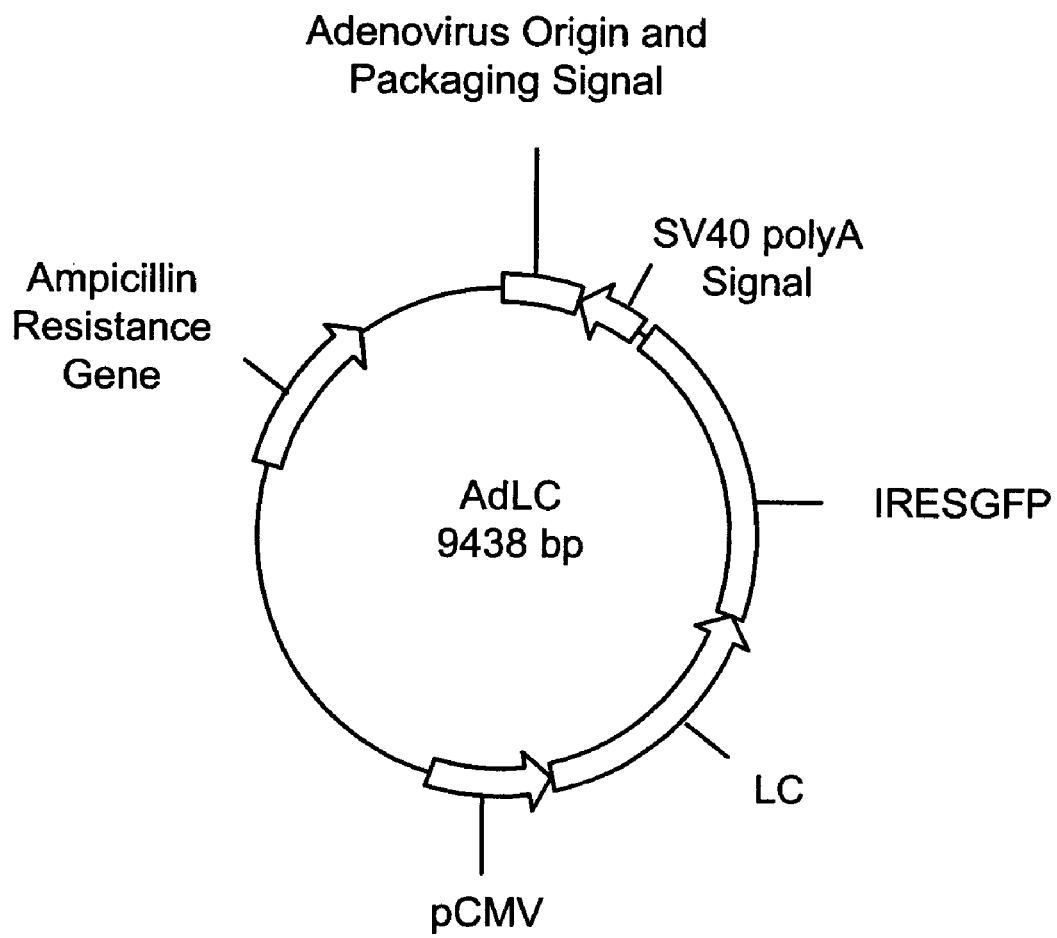
FIG. 2 is a schematic illustration of a shuttle plasmid used to construct an adenovirus vector containing a gene encoding a *clostridial* neurotoxin light chain peptide.

Construction of a Vector (AdLC) Containing a Gene Encoding the Light Chain of Tetanus Toxin (LC) and Expression of the LC Gene from the AdLC A 1496 base pair synthetic gene having a nucleic acid sequence of GenBank Accession No. L19522 (LC gene) encoding the light chain of a tetanus toxin peptide (LC peptide) is cloned into an adenovirus vector pACCMVpLpA(−)loxP.SSP under the control of a cytomegalovirus (CMV) promoter. For easier identification of gene expression in vitro and in vivo, an internal ribosome entry site (IRES)-driven green fluorescent protein (GFP) sequence is cloned downstream of the LC gene into the pACCMVpLpA(−)loxP.SSP vector. An attenuated adenovirus vectors (the E1A, E1B, and E3 regions of the adenovirus (wildtype Ad5) genome are deleted) is produced through in vitro recombination with the sub360loxp cosmid as described below. The resulting vector is named pAdLC and is schematically illustrated in FIG. 2. Two more vectors are produced and purified following the same protocol and are used as control vectors. The first vector contains a beta-galactosidase reporter gene LacZ (LacZ gene) under the control of a CMV promoter and is named AdLacZ. The second vector contains a GFP reporter gene under the control of a rous sarcoma virus (RSV) promoter and is named AdGFP. The AdLC vector, AdLacZ vector, and AdGFP vector are purified by standard cesium chloride purification protocol (See Graham F., Prevec, L. "Methods for Construction of Adenovirus Vectors," *Mol. Biotechnol;* 3: 207-220 (1995), which is incorporated by reference herein).

Figure 6:
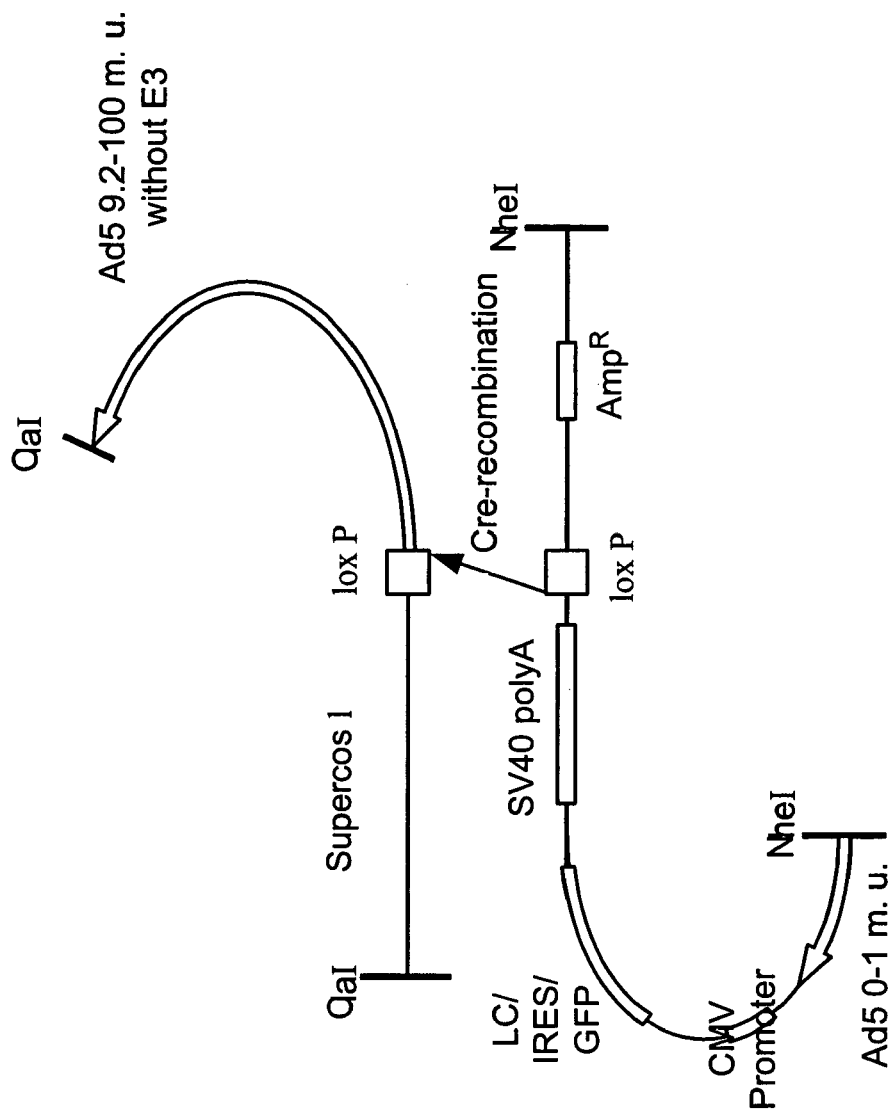
FIG. 6 is a schematic illustration of an in vitro Cre-LoxP recombination. The 3' end adenovirus 360 is excised from the cosmid cSub360 and recombined in vitro with the 5' end of Ad5 containing the light chain peptide and GFP expression cassette. Cre recombinase recognizes the loxP sequence in vitro.

A first generation adenovirus is generated from the pAdLC vector through Cre-mediated in vitro recombination between the pAdLC vector and a 3' adenoviral sequence according to standard published protocol (See Aoki K. et al. "Efficient generation of recombinant adenoviral vectors by Cre-lox recombination in vitro," *Mol. Med;* 5:224-231 (1999), which is incorporated by reference herein). FIG. 6 illustrates this process.

The first generation adenovirus is amplified by propagation in HEK 293 cells. To produce recombinant adenovirus, 5 micrograms (µg) of Cre treated DNA are transfected into 60 millimeter (mm) dishes of HEK 293 ells. These cells express the E1 region deleted from the recombinant viruses. When cytopathic effect is noted in the HEK 293 cells (7-9 days), a crude lysate is made from the cells. This lysate is then used to infect a 100 mm dish of HEK 293 cells. Crude lysates of the recombinant viruses AdLC, AdLacZ, and AdGFP are doubly plaque purified. PCR is used to confirm insertion of the fragments in the virus. These vectors are amplified and purified.

Figure 4:
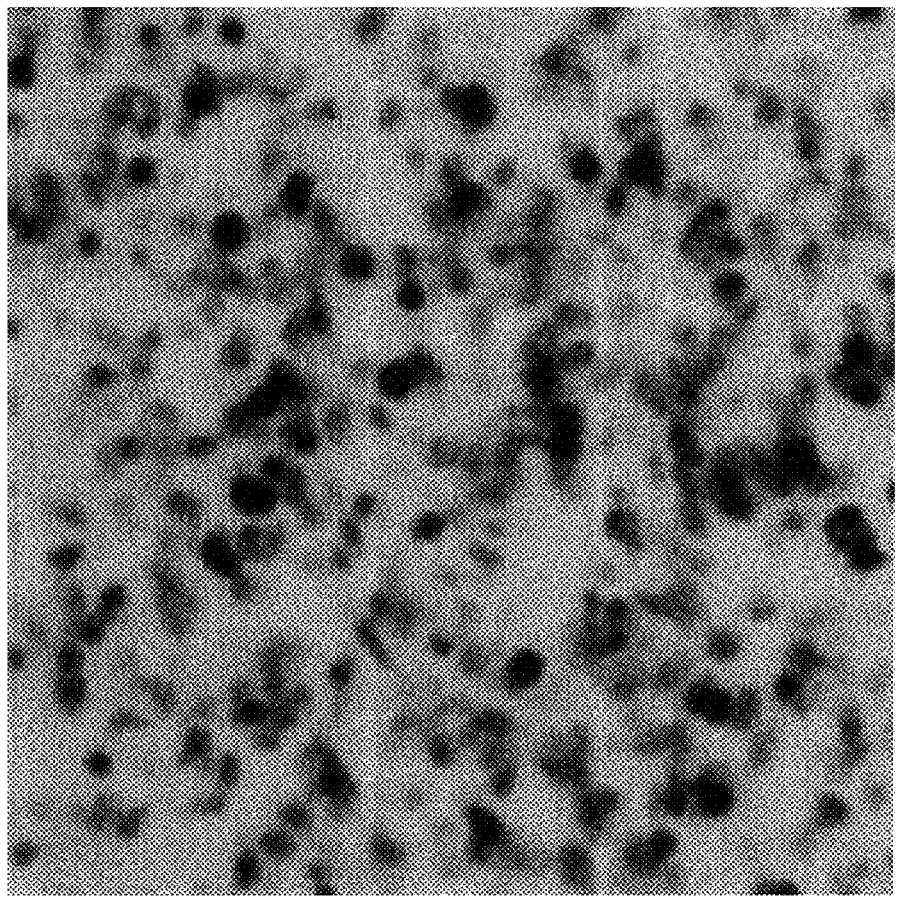
FIG. 4 is a photograph of a fluorescent microscopy of HEK 293 cells 24 hours after exposure to a vector containing a gene encoding a *clostridial* neurotoxin light chain peptide, an internal ribosomal entry site, and the green fluorescent protein (GFP) gene. It demonstrates that 100% of cells express the gene encoding the *clostridial* neurotoxin light chain peptide and GFP reporter gene.

To further confirm that the AdLC vector is capable of inducing production of the LC gene, HEK 293 cells infected with AdLC and AdLacZ are imaged under a fluorescent microscope. FIG. 3 shows the fluorescent microscopy of HEK293 cells 24 hours after exposure to (A) AdLacZ and (B) AdLC. The high percentage of fluorescent cells indicates that the AdLC is active. FIG. 4 shows that four days following infection with AdLC almost 100% of the cells show evidence of the LC gene.

Figure 5:
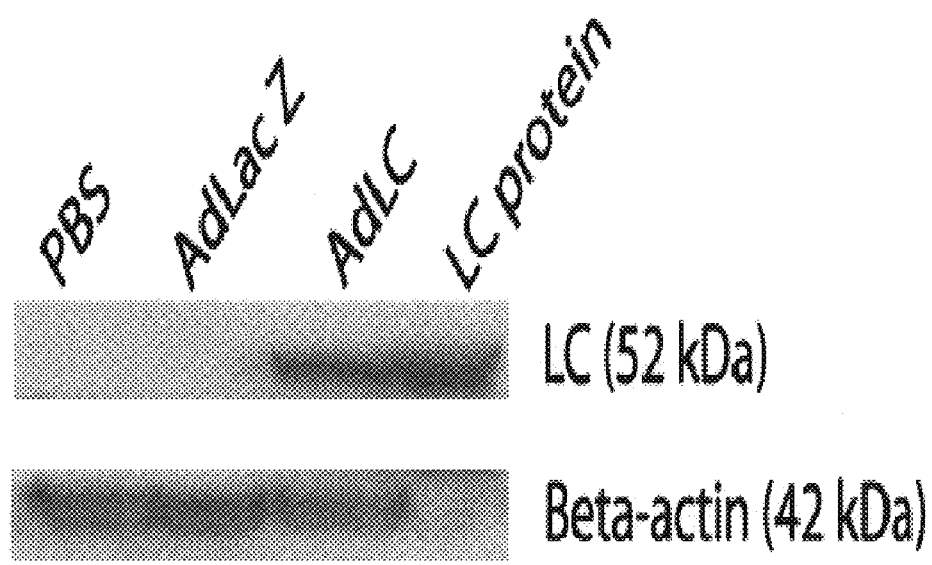
FIG. 5 is a photograph illustrating an anti-*clostridial* neurotoxin light chain peptide and anti-β actin western blot. This blot demonstrates that a vector causes production of the *clostridial* neurotoxin light chain peptide.

To confirm the expression of the LC gene from the first generation adenovirus vector, HEK 293 cells are infected with the AdLC vector and an anti-LC western blot is performed on cell lysates from the infected HEK 293 cells using primary antibodies against the LC peptide (Medizinische Hochschule Hannover, Del.). A BCA protein assay (Pierce, Rockford, Ill.) is used on all samples prior to loading in order to confirm equal protein concentration across lanes. The western blot is also probed with an anti-β-actin primary antibody to confirm equal protein loading. Lysates from other HEK 293 cells exposed to PBS or AdLacZ are run as negative controls and recombinant LC peptide is run as a positive control. As shown in FIG. 5, a 52 kDa LC peptide is expressed in HEK 293 cells infected with AdLC but not in the negative controls. B-actin staining shows no apparent protein loading variations between the experimental conditions (cells exposed to AdLC), negative conditions (cells exposed to PBS or AdLacZ) and control conditions (recombinant LC peptide).

Example 2

Figure 7:
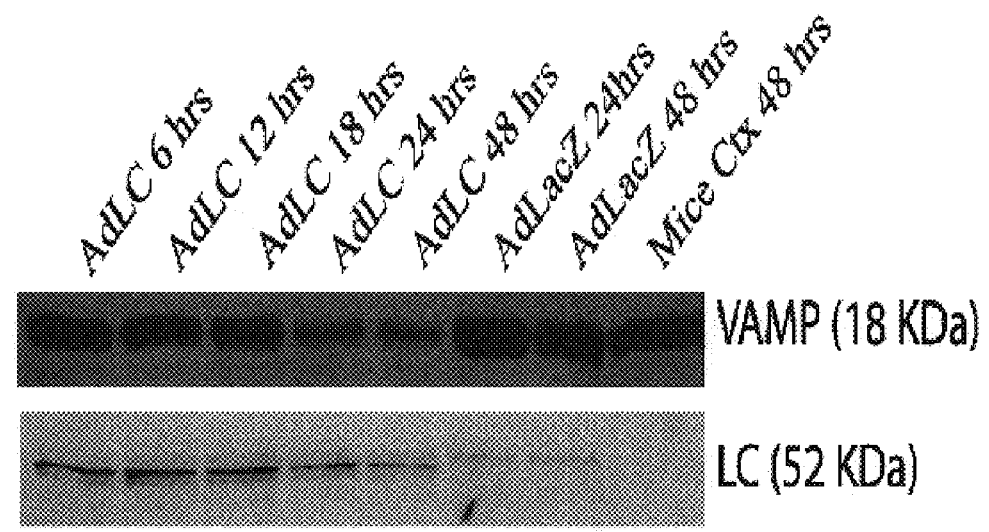
FIG. 7 is a photograph of a western blot using an antibody against VAMP. Mouse cortex protein is exposed to 5 μg of lysate from PC12 cells infected with a vector containing a tetanus toxin light chain peptide (AdLC) or a vector containing a LacZ reporter gene (AdLacZ) at an moi of 5 for different time intervals prior to western blotting. A western blot using an antibody against VAMP showed a progressively decreased density of VAMP bands corresponding to longer incubation periods in AdLC lysate. The same blot stripped and re-probed with an antibody against the light chain peptide (LC) shows consistent levels of the 52 kDa protein of LC in AdLC lysates, controlling for protein loading in these conditions, and reveals no LC peptide in the AdLacZ or mouse cortex protein controls.
Figure 8:
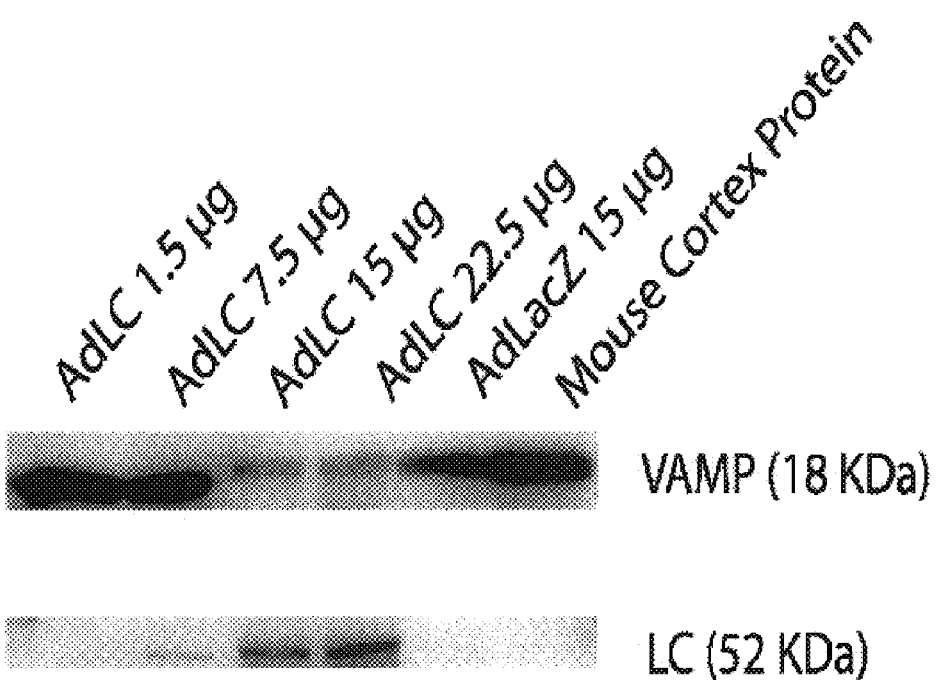
FIG. 8 is a photograph of a western blot using an antibody against VAMP. Mouse cortex protein is exposed to a series of concentrations of lysate from PC12 cells infected with AdLC or AdLacZ at 37° C. for 2 hours. A western blot using an antibody against VAMP shows a progressively decreased density of VAMP bands corresponding to the higher concentration of AdLC PC12 cell lysate. Reprobing the blot with anti-LC reveals increasing concentrations of LC protein corresponding to decreasing VAMP band density. LC protein is absent from mouse cortex protein and the AdLacZ lysate condition.

Construction of AAV Vectors (AAVCMVLC and AAVTet-onLC) Containing a Gene Encoding the Light Chain of Tetanus Toxin (LC) and Expression of the LC Gene from these Vectors A pTRUF-5 plasmid (Nicholas Muzyczka, University of Florida, Gainsville) is used for the creation of a recombinant adeno-associated virus (AAV-GFP). pTRUF-5 contains gene for GFP under control of CMV promoter. In order to make adequate room in the pTRUF-5 plasmid, the neo resistance sequence is removed by restriction digest. A separate restriction digestion is performed with Not I to remove the GFP sequence. The sequence of the LC-IRES-GFP is cloned into pTRUF-5 between the Not I sites (such resulting vector being named pTRUF-5LC). Restriction mapping is conducted to ensure the proper orientation of the LC gene. This strategy resulted in the creation of an AAV vector containing the LC gene and IRES-GFP sequences under the control of the CMV promoter with an associated 3' polyA sequence.

For harvesting viruses, triple transfection is conducted in twenty 150 mm plates of 293 cells at 70-80% confluence. To insert the LC gene into the AAV (such resulting vector being named AAVCMVLC-IRESGFP), cells are exposed to the pro-viral sequence, pXX2 (Jude from University of NCcarrying the rep and cap genes of AAV with no ITRs, and the pXX6 (a helper plasmid) (Jude) containing the adenoviral genes necessary for rAAV production, and 25 μg of plasmid DNA for pTRUF-5LC. pXX2, and pXX6 are EtOH precipitated and re-suspended individually in 18 ml of sterile water with 2 ml of 2.5 M of $CaCl_2$. This solution is added to pH 7.05 0.05 M HEPES, 02.8 M NaCl, and 1.5 mM $Na_2HPO_4$ and 20 minutes later the mixture is observed for precipitation. 2 ml of each precipitate are added to each plate of cells. Cells are fed with Iscoves' modified eagles medium with 10% fetal bovine serum (FBS) and no antibiotics. The viral band is isolated from the crude lysate by CsCl gradient ultracentrifugation and antibiotics. The viral band is isolated from the crude lysate by CsCl gradient ultracentrifugation and dialyzed into PBS with sucrose as a cryoprotectant. Viral titer is estimated with slot blots.

A tetracycline (Tet)-inducible LC gene expression system is created by replacing the CMV promoter in pTRUF-5LC with the Tet-response element (TRE). A second expression cassette is inserted consisting of the CMV constitutive promoter driving expression of the reverse tetracycline-controlled transactivator (rtTA). This plasmid, pTRUF-5Tet-onLC, is used to create an adeno-associated virus (AAV) vector (AAVTet-onLC) through the triple transfection method described above. In cells infected with AAVTet-onLC, LC expression is under the control of the TRE promoter. The gene for the regulatory protein, rtTA, is under the control of the CMV constitutive promoter. In the presence of the tetracycline derivative, doxycycline (Dox), TRE activation leads to the expression of LC gene. In contrast, the absence of Dox silences LC gene expression. To test Dox dependent control of LC gene expression, HEK293 cells are infected with AAVTet-onLC virus. After incubation with Dox (AAVTetonLC Dox-2 and AAVTetonLCDox-3) and without Dox (AAVTetonLC No Dox-2 and AAVTetonLC No Dox-3), the infected HEK293 cells are harvested for western blot using an antibody against LC protein (FIG. 25). FIG. 25 shows LC gene expression by AdLC (referred to as AdCMVLC-IRESGFP) and AAVCMLV-IRESGFP as well AAVTetonLC in the presence but not the absence of Dox.

Example 3

LC Gene Expression Results in Cleavage of the VAMP-1 SNARE Protein

Differentiated pheochromocytoma-12 (PC12) cells induced with nerve growth factor (NGF) (Sigma Aldrich. St. Louis, Mo.) at a concentration of 50 ng/ml are infected with AdLC, AdLacZ or AdGFP vectors (see Example 1) at a m.o.i. of 5 for 48 hours. The PC12 cells are lysed and the resulting cell lysate is used as a source of LC peptide and control peptide for the subsequent enzymatic digestion of mice cortex tissue containing VAMP-1.

Five μg of protein extracted from mouse cortex protein containing VAMP-1 is incubated with peptides obtained from PC12 cells infected with AdLC, AdLacZ or AdGFP in a light chain reaction buffer (5 mM HEPES, 0.3 M Glycine, 0.3 M NaCl, 0.02% $NaN_3$, pH 7.4) at 37° C. A concentration-response curve of cortical VAMP-1 digestion is carried out with 1, 5, 10, 15, and 20 microliters (μl) of cell lysate containing AdLC. To test time-dependence of VAMP-1 digestion, incubation is also performed for 6, 12, 18, 24, and 48 hours with 5 μg of cell lysate from cells infected with AdLC and for 24 to 48 hours with cell lysate from cells infected with AdLacZ.

Following incubation, each reaction mixture is loaded on a PAGE gel and western blots are performed using any antibody against VAMP-1 (Santa Cruz Biotechnology, Santa Cruz, Calif.). As in Example 1, a BSC protein assay is used on all samples prior to loading in order to confirm equal protein concentrations across lanes.

The density of the 18 kDa mouse brain VAMP-1 band deteriorates as a function of the duration and incubation with AdLC cell lysates, but not with AdLacZ cell lysates, indicating cleavage of VAMP-1 by AdLC. FIG. 7 illustrates that the VAMP-1 band shows reduced density as a function of the duration of exposure to protein taken from PC12 cells exposed to AdLC. The VAMP-1 bands also show reduced density at higher concentrations of the AdLC cell lysate as illustrated in FIG. 8 suggesting a concentration-dependent LC peptide activity. The blots are stripped and re-blotted to confirm the presence of LC peptide using an anti-LC antibody. Such a re-probing of the same blot with an anti-LC antibody reveals a consistent level of LC peptide in AdLc cell lysates confirming the deterioration of VAMP-1 band density is not caused by the variation of the AdLC cell lysate used in the reaction mixture. This band also serves to confirm equal protein loading in the time-course experiment. No signals specific to the anti-LC antibody is detected in AdLacZ cell lysates or mouse cortex protein as illustrated in FIG. 7 and FIG. 8.

Example 4

Delivery of LC Gene in Vivo into Rat Spinal Cord

Adult female Sprague-Dawley rats (Harlan, Indianapolis, Ind.), weighing 150-250 grams are randomly assigned to four groups and are trained to run on an Economex rotarod apparatus (Columbus Instruments, Columbus, Ohio) for one week prior to surgery using standard techniques known in the art (See Acsadi G. et al. "Increased survival and function of SOD1 mice after glial cell-derived neurotrophic factor gene therapy," *Hum Gene Ther;* 13: 1047-59 (2002), which is incorporated by reference herein). The day prior to surgery, locomotion is assessed on a 21-point Basso-Beattie-Bresnahan (BBB) scale (See Basso D., Beattie M., Bresnahan J. "A sensitive and reliable locomotor rating scale for open field testing in rats," *J. Neurotrauma;* 12: 1-21 (1995), which is incorporated by reference herein). Rats are anesthetized with isoflurane (3% in $O_2$) and placed in a Kopf stereotaxic frame (David Kopf Instruments, Tujunga, Calif.) to restrict movement. A dissecting microscope (Stereozoom 6; Leica, Buffalo, N.Y.) is used in all surgical procedures. A 2 centimeter midline incision is made over the lumbar lordosis of all rats and the L2 spinous process is identified and removed with a rongeur without tearing or otherwise damaging the underlying dural membrane or traumatizing the spinal cord. The dura mater is then incised with a microscalpel. Spinal cord injections are performed with an oocyte microinjector (Nanoject; Drummond, Broomall, Pa.) mounted with glass micropipettes. A glass micropipette puller (PP083; Narishige, Tokyo, Japan) is used to create tapered tips on micropipettes, which are then beveled to 100 microns (µm) under microscopic visualization. Micropipettes are advanced through the pia mater into the spinal cord parenchyma to a depth of 2 mm using a micromanipulator (N-152; Narishige, Tokyo, Japan) 1 mm lateral to midline.

The first group of rats (n=4) receive 10 µl injections of AdLC (titer $7.8 \times 10^9$ PFU/ml). The second group of rats (a control group) receive 10 µl of AdGFP (n=4) (titer $8.0 \times 10^9$ PFU/ml). The third group of rats (a control group) receive 10 µl of AdLacZ (n=4) (titer $8.0 \times 10^9$ PFU/ml). The fourth group of rats (a control group) receive 10 µl of diluted AdLC (n=4) (titer $7.8 \times 10^8$ PFU/ml) (AdLC/10). A separate independent blinded experiment comparing AdLC to AdGFP (n=8). Injections are performed gradually over a 15 minute period to minimize reflux of the viral solution and spinal cord trauma. The vectors are also injected on the contralateral side of the spinal cord in the same manner as described above.

Example 5

Expression of LC Gene in Spinal Cord

Five days after injection, rats from Example 4 are euthanized with intraperitoneal pentobarbital, and undergo transcardiac perfusion with 2% paraformaldehyde (Sigma-Aldrich Co, St Louis, Mo.). Spinal cords are dissected, post-fixed overnight in 2% paraformaldehyde at 0° C. for four hours and blocked and transferred to a 20% sucrose solution for 24 hours.

To detect beta-galactosidase, the spinal cord tissue from rats injected with AdLacZ, is rinsed three times in lacZ rinse (2mM MgCl2, 0.1 mg/ml Na deoxycholate, $\frac{1}{5000} \times$ Triton-X in PBS), then three times in PBS at 0° C. for five minutes each and incubated in X-gal stain (β-gal kit, Invitrogen Life Technologies, Carlsbad, Calif.) for twelve hours at 37° C. Tissue is then counterstained with cytoplasmic eosin.

Spinal cord tissue is cut serially in 20 µm sections using a Jung Frigocut 2800 cryostat (Leica Microsystems, Nussloch, Germany) and mounted on pre-cleaned superfrost plus microslides (VWR Scientific, West Chester, Pa.). Tissue sections are digitally photographed and the area of tissue staining with beta-galactosidase is quantified with NIH image software.

GFP expression is detected under a fluorescent microscope. Motor neurons expressing GFP or LacZ are histologically identified on sections of lumbar spinal cord using established morphological criteria. Tissue sections are compared for qualitative differences indicative of structural damage.

Figure 9:
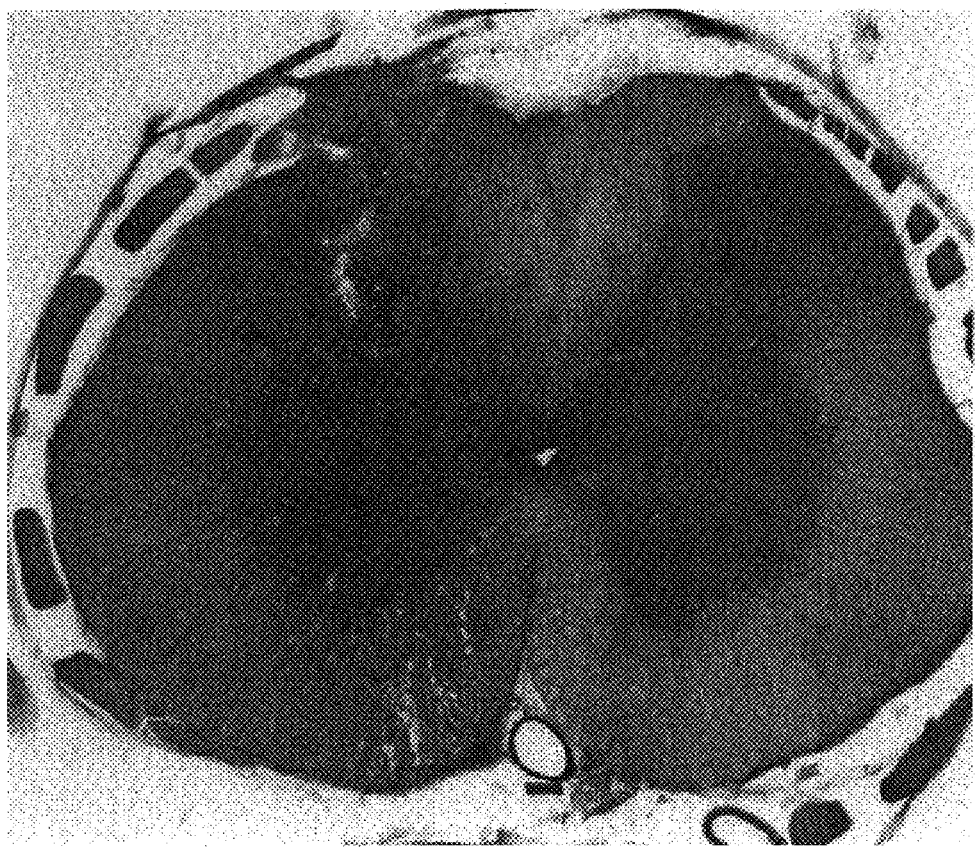
FIG. 9 is a photograph of a coronal section of a rat spinal cord expressing the β-galactosidase gene five days after injection with a vector containing a LacZ reporter gene.
Figure 10:
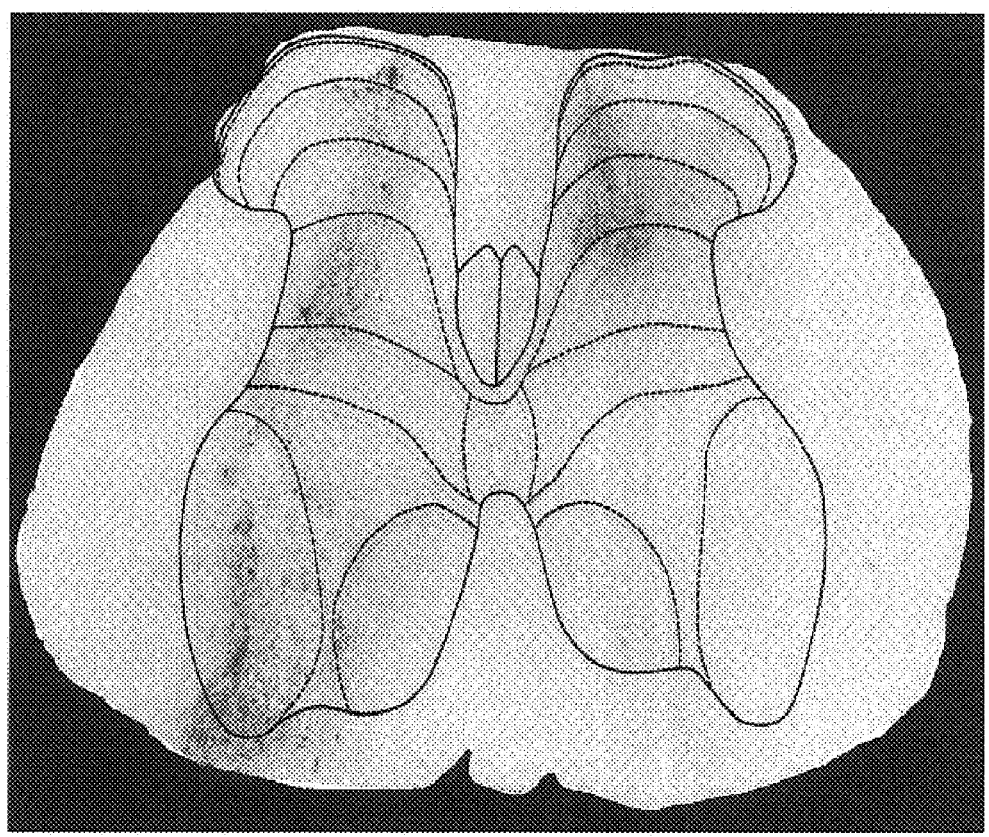
FIG. 10 is a photograph of a stained coronal section of a rat spinal cord five days after injection with a vector containing a gene encoding a tetanus toxin light chain peptide and the GFP gene. A morphed atlas of spinal cord anatomy is overlain to provide a context for the GFP distribution.

Such histological analysis of spinal cords confirms activity of the LC-IRES-GFP expression cassette in all groups of rats injected with AdLC. The spinal cords of the group of rats injected with AdLacZ have abundant neuronal β-galactosidase (β-gal) staining (See FIG. 9), while the spinal cord of the group of rats injected with AdLC have abundant neuronal green fluorescence (See FIG. 10). Gene expression occurs predominantly in the spinal cord gray matter. The majority of neurons are transduced in the region of injection.

Example 6

Expression of LC Gene in Brain Stem and Inhibition of Neurons with the Brain Stem as a Result of Such Expression A rat startle system is used to determined whether AdLC can achieve specific inhibition of a subset of neurons within the brainstem. The rat acoustic startle reflex (ASR) is a trisynaptic reflex consisting of spiral ganglion cells within the cochlea, cochlear root neurons, neurons within the nucleus reticularis pontis caudalis (PnC) and spinal motor neurons. The startle response is modulated by the amygdala via a multisynaptic pathway featuring the deep layers of the superior colliculus (dSC).

A total of 36 rats are divided into three experimental groups: Rats administered AdLC, rats administered AdGFP, and rats administered PBS. Startle responses are evoked by a 50 ms white noise burst and are measured by an accelerometer affixed to the bottom of each test cage containing the rats. Bilateral dSC of each rat is injected stereotactically (AP-6.8, ML=/-1.5, DV-5.0) with two µl of AdLC, AdGFP ($8 \times 10^7$ PFU/ml) or PBS under isoflourane anesthesia. Post-operatively, the fear potentiated startle of each rat is measured by the accelerometer.

Figure 21:
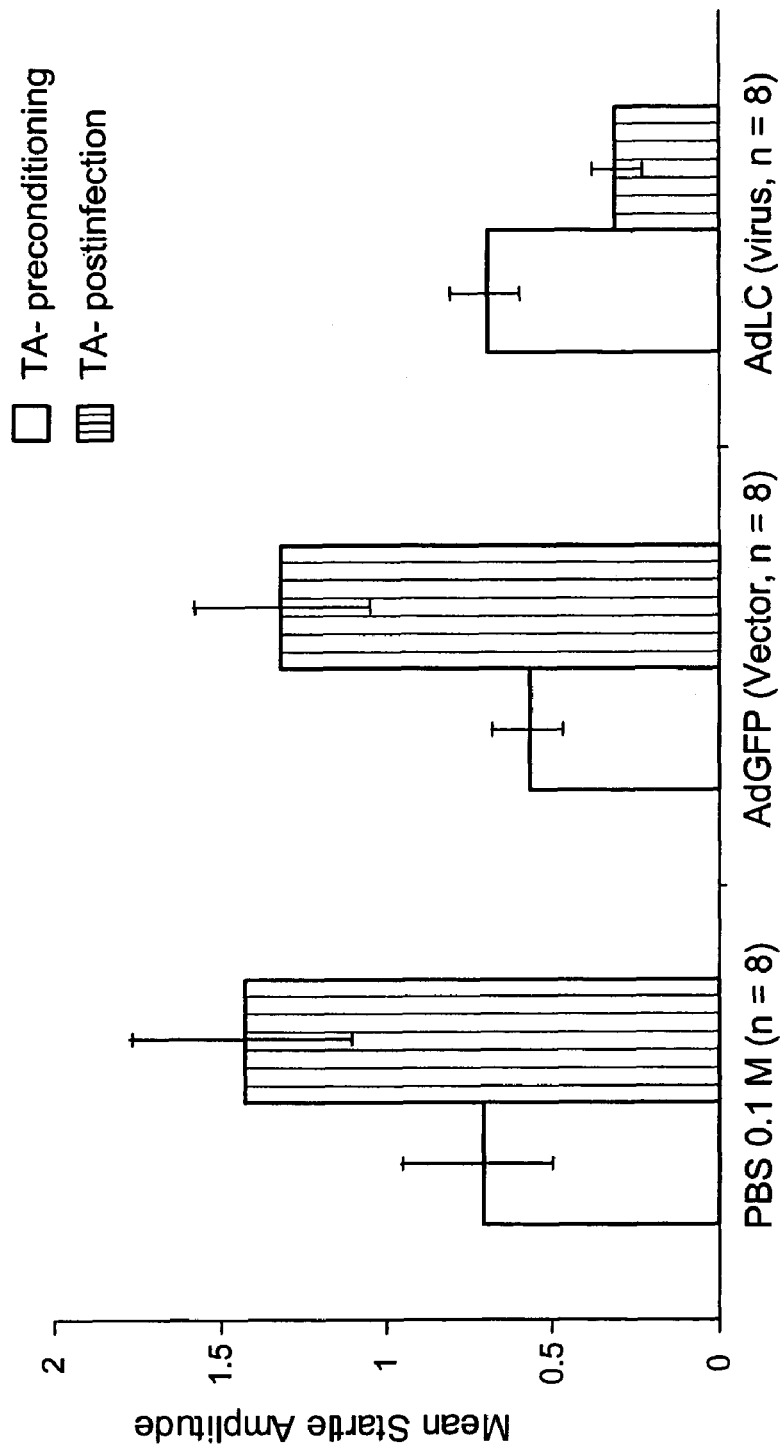
FIG. 21 is a chart depicting the mean startle amplitude of rats injected with AdLC, PBS, or AdGFP. This chart indicates that expression of a gene encoding a clostridial neurotoxin light chain peptide in the deep layers of the superior colliculus (dSC) inhibits the acoustic startle reflex.
Figure 22:
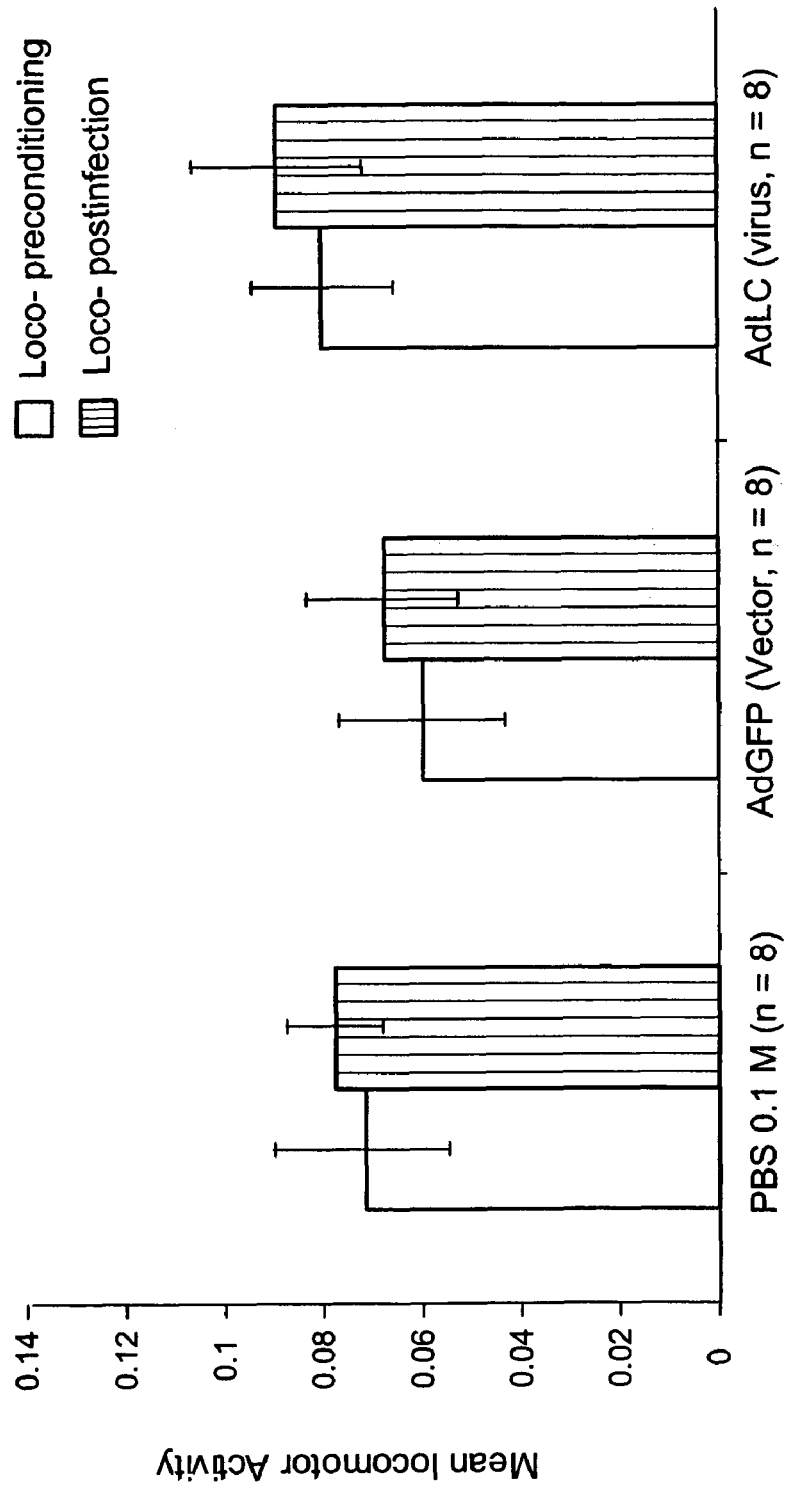
FIG. 22 is a chart depicting the mean locomotor activity of rats injected with AdLC, PBS, or AdGFP. This chart indicates that expression of a gene encoding a *clostridial* neurotoxin light chain peptide in the dSC does not affect the rats' spontaneous motor activity.
Figure 23:
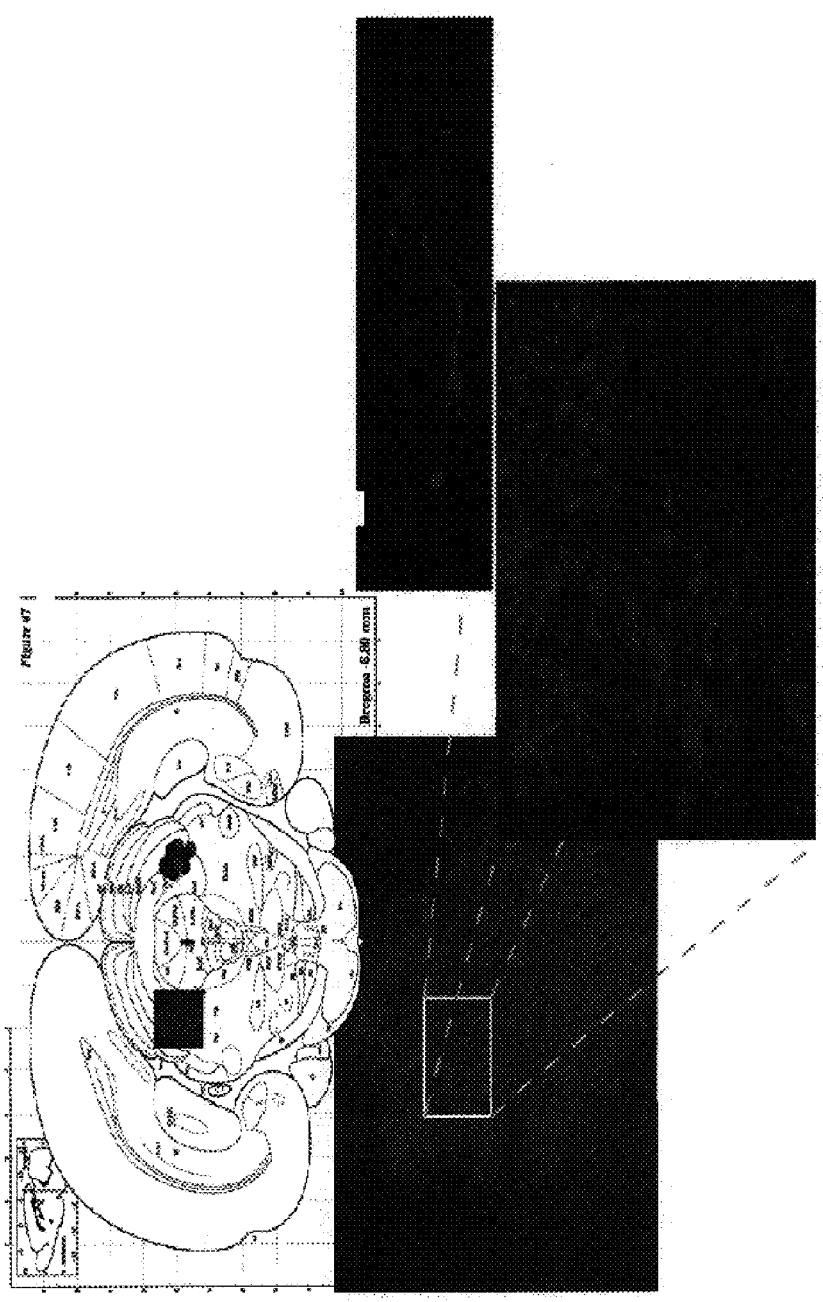
FIG. 23 illustrates the distribution of expression of a gene encoding a clostridial neurotoxin light chain peptide in the dSC after a 2 microliter stereotactic injection.

FIG. 21 shows that acoustic startle significantly diminishes in rats that are administered AdLC 11 days post-injection compared with AdGFP and PBS control groups. Spontaneous motor activity as measured by cage accelerometer is not affected (FIG. 22). Histology confirms expression of GFP in the brainstems of rats administered AdLC and rats administered AdGFP. Mean distribution of expression is 1.6 mm and is limited to the injection site (FIG. 23).

Such results of inhibition of acoustic startle without changes in spontaneous motor activity, level of arousal, or respiration indicate a specific inhibition of dSC function without alteration of synaptic transmission in surrounding brainstem structures.

Example 7

Injection of LC Gene in Vivo Results in Inhibition of Sensorimotor Function as Assessed by Locomotor BBB Scale Rats from Example 4 are allowed to recover for 24 hours following surgery. Because adenovirus gene expression is delayed in the spinal cord, rats showing significant immediate postoperative hindlimb dysfunction are assumed to have a spinal cord injury related to surgery and are therefore excluded from further analysis. Based on these criteria, two rats are eliminated from the study (See Boulis N et al., "Adenoviral nerve growth factor and β-galactosidase transfer to spinal cord: A behavioral and histological analysis," *J. Neurosurg;* 90:99-108 (1999), which is incorporated by reference herein. An investigator blinded to the treatment conditions assesses animal motor function over five sequential days using the locomotor BBB scale. The criteria for rating on the 21-point scale (21=normal motor function, 0=no observable hindlimb movement) are adapted from Basso D., Beattie M., Bresnahan J. "A sensitive and reliable locomotor rating scale for open field testing in rats," *J. Neurotrauma;* 12: 1-21 (1995), which is incorporated by reference herein. Before surgery, all rats have a BBB score of 21 reflecting normal gait.

Figure 12:
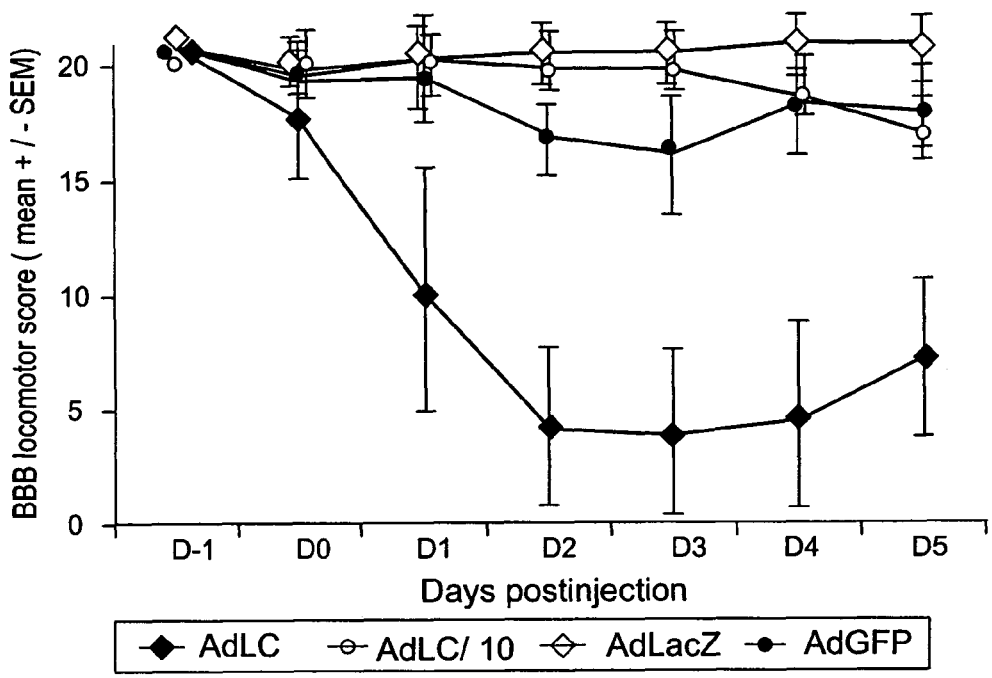
FIG. 12 is a graph plotting the BBB scores of rats injected with AdLC, a diluted concentration of a vector containing a tetanus toxin light chain peptide (AdLC/10), AdLacZ, or a vector containing a GFP reporter gene (AdGFP) over a five day observation period.

Following injection, the first group of rats that are injected with AdLC bilaterally develop a bilateral flaccid hindlimb paralysis 72 hours after injection (See FIG. 11A). FIG. 11A shows such a rat dragging his hindlimbs with the palmar surface of the foot visible bilaterally. In contrast, hindlimb function, including weight bearing and posture, is preserved in the third group of rats that are injected with AdLacZ and the motor function of such rats is fully recovered within 24 hours (See FIG. 11B). FIG. 11B shows such a rat bearing weight on his flexed hindlimb. In this posture, the palmar surface is downward, bearing weight, and is therefore not visible. Following recovery from anesthesia, the first group of rats exhibit a mean score of 17.8+/−2.92 (+/−SEM) on the BBB scale, which is not statistically different from the second group of control rats injected with AdGFP, who exhibit a mean score of 19.6+/−0.33 (+/−SEM) and the third group of control rats injected with AdLacZ, who exhibit a mean score of 19.66+/−0.67 (+/−SEM). 48 hours after vector administration, the first group of rats injected with AdLC exhibit a mean BBB score of 4+/−3.67, in comparison to the second and third control rats injected with AdGFP and AdLacZ, respectively, who exhibit mean scores of 17+/−1.52 and 20.66+/−0.33, respectively. FIG. 12 depicts the reduction in motor function as reflected by decreased BBB scores up to five days after injection in the first group of rats injected with AdLC, but not in the second and third group of rats injected with AdLacZ and AdGFP respectively, or the fourth group of rats injected with one logarithmic lower concentration of AdLC (AdLC/10).

A score of 4 on the BBB scale reflects only a slight movement of the three joints of the hindlimbs, while a score above 17 reflects consistent plantar stepping, consistent forelimb-hindlimb coordination and frequent toe clearance during forward limb advancement. A decrease of 13 points on the BBB scale after administration of AdLC reflects a severe impairment of the hindlimb motor function induced by spinal cord injection of a concentrated suspension of AdLC. Two-way ANOVA statistics demonstrate a highly significant difference in BBB score following AdLC, AdGFP, and AdLacZ administration ($P<0.0001$, $F=30$, $F=1.92$, df 18).

Example 8

Injection of LC Gene in Vivo Results in Inhibition of Sensorimotor Function as Assessed by Rotarod Assay A second motor function assay (the "rotarod assay") tests the maximal speed (Vmax) and the amount of time at which rats from Example 4 are able to maintain balance on an Economex rotarod apparatus, which is a spinning dowel. The Economex rotarod apparatus has previously been utilized to efficiently assay the behavioral impact of progressive motor neuron disease (See Acsadi G. et al. "Increased survival and function of SOD1 mice after glial cell-derived neurotrophic factor gene therapy," *Hum Gene Ther;* 13: 1047-59 (2002), which is incorporated by reference herein). Performance on the rotarod tests both forelimb and hindlimb function as well as balance and requires intact sensorimotor function in all limbs, thus providing an objective and investigator-independent assessment of hindlimb motor performance. Following establishment of baseline motor performance at 5 rpm, the rotarod is accelerated by 0.1 rpm/second increments and the time required for the rat to fall off the rotarod is observed. The maximal speed (Vmax) at which the rat is able to remain on the rotarod is calculated with the following formula:

$$V\max=(ta)+s$$

t=the time required for the rat to fall from the rotarod, a=the acceleration of the rotarod apparatus and, s=the start up speed.

As with the BBB assessments disclosed in Example 7, motor performance on the rotarod apparatus is assessed daily for five consecutive days after vector administration.

Figure 13:
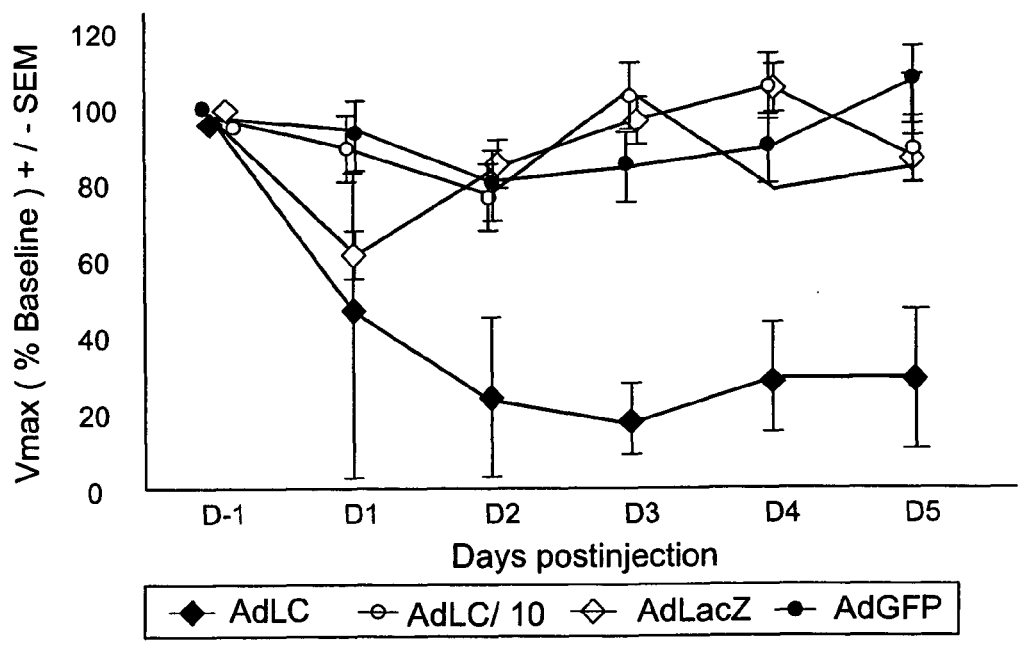
FIG. 13 is a graph plotting the Vmax scores, as measured on a Rotarod apparatus, of rats injected with AdLC, AdLC/10, AdLacZ, or AdGFP over a five day observation period.

The first group of rats injected with AdLC reach only 0 to 58% of their pre-injection Rotarod performance in an observation time of five days and are only capable of reaching 23.75% of their pre-injection Vmax baseline two days after vector administration (See FIG. 13). The third group of rats injected with AdLacZ reach up to 90% of their pre-surgical performance in an observation time of five days. Two-way ANOVA statistics demonstrate a significant decrease in rotorod Vmax in the first group of rats injected with AdLC compared to the fourth group of control rats injected with a diluted concentration of AdLC (AdLC/10), the second group of control rats injected with AdGFP and the third group of control rats injected with AdLacZ ($P<0.0001$, $df=3$, $F=11.23$). The additional group of rats that received $8\times10^6$ PFU/ml of AdLC show no change in locomotion on any of the five days of testing.

Specifically, the second, third and fourth group of rats maintain their motor function up to five days postsurgically while the first group of rats start to develop significant hindlimb paresis. These results confirm LC gene expression dependent deterioration in hindlimb sensorimotor function. Further, logarithmic decrease in viral concentration significantly ($p<0.05$) delays the onset and amplitude of hindlimb paresis. Therefore, LC gene expression in spinal cord induces titer-dependent motor dysfunction in rats.

Example 9

Injection of LC Gene in Vivo Results in Inhibition of Synaptic Transmission

To demonstrate that the observed sensorimotor dysfunction in vivo as disclosed in Examples 6-8 is mediated by impaired synaptic transmission at the neuromuscular junction, evoked electromyogram (EMG) is measured in two groups of rats after vector administration into the spinal cord.

Specifically, to test the response of gastrocnemius muscle to sciatic nerve stimulation following vector administration, 10 µl of AdLC as described in Example 1 is injected bilaterally into the lumbar spinal cord of the first group of rats (n=3) and 10 µl of AdGFP as described in Example 1 is also injected bilaterally into the lumbar spinal cord of a experimental second group of rats (n=3). Following delivery of the viruses, all rats are allowed to recover and ambulate.

All rats are then anesthetized with isoflurane and placed under a dissecting microscope. The skin is incised 2-3 centimeters lateral to the lumbar spine. The muscle planes are separated to avoid injury to blood vessels or nerves and the sciatic nerve and a large area of gastrocnemius muscle is exposed. A subminiature electrode (Model AH50-1650, Harvard Apparatus, Holliston, Mass.) is applied on the exposed sciatic nerve and secured in place. Gastrocnemius EMG responses are obtained via a pair of surface electrodes (Sensormedics, Anaheim, Calif.) with an exposed contact diameter of 2 millimeters. The electrodes are placed 1 centimeter apart and secured to the surfaces of the exposed muscle body.

EMG is evoked by electrical stimulation through the subminiature electrode encompassing the exposed sciatic nerve. Square-wave, constant current pulses are delivered with a pulse width of 90 µs using a Grass Model S88 stimulator connected to a Model SIU7 stimulus isolation unit (Grass-Telefactor, West Warwick, R.I.). Trains of stimuli are delivered with intra-train pulse rates of either 5 pulses per second (pps) or 88 pps. The 80 pps condition is included to observe the pattern of response extinction. Current amplitude is increased by 0.1 mA intervals in order to measure the threshold for evoked motor response in the gastrocnemius. For the purpose of analysis, the root mean square (RMS) value for the evoked response to each stimulus pulse is calculated. These values are then 5 bin averaged (each point representing approximately 62 milliseconds and plotted over a 60 second period of stimulation).

Figure 14:
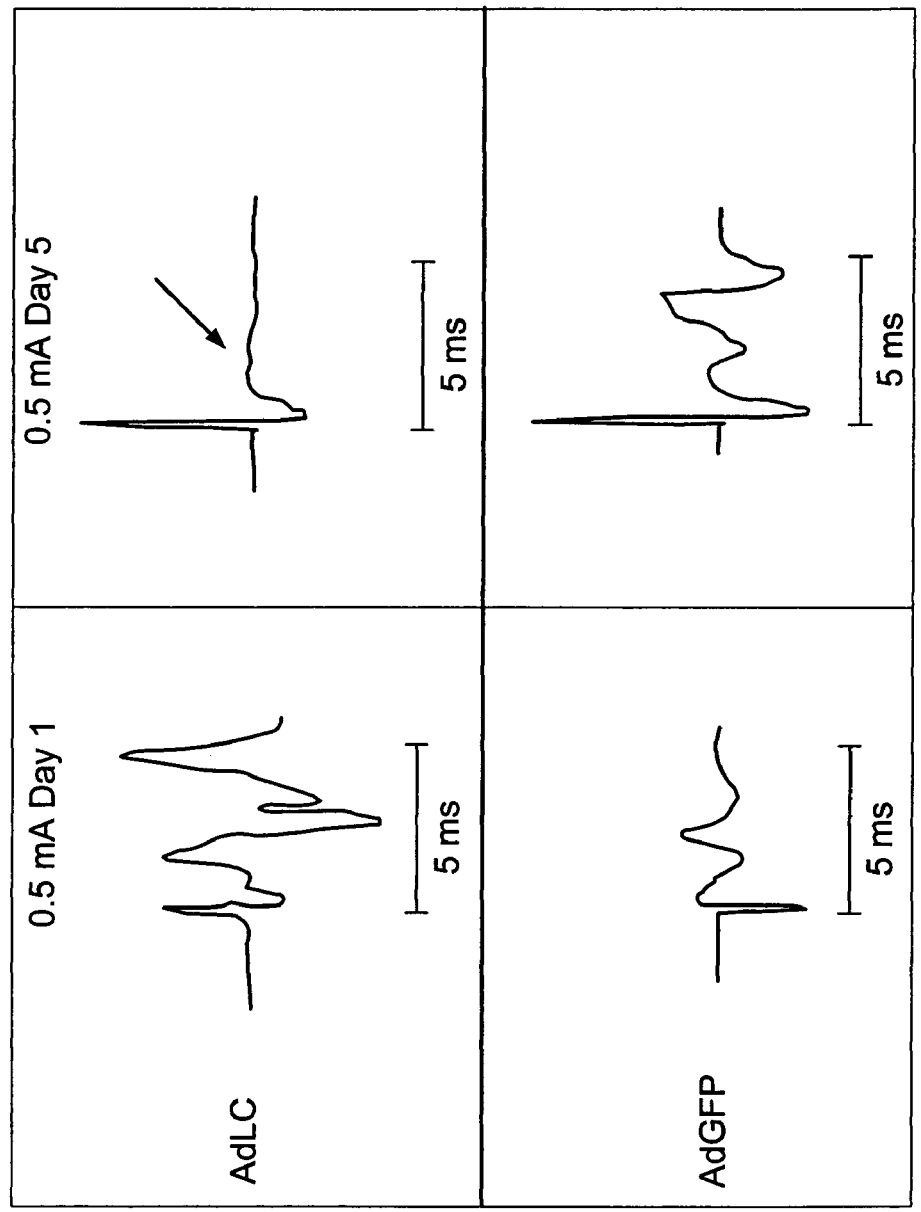
FIG. 14 depicts evoked gastrocnemius EMG results of sciatic nerve stimulation in rats injected with an vector containing a tetanus toxin light chain peptide (AdLC) and rats injected with AdGFP on day one of injection and day five thereafter.

The evoked motor response recorded across days one and five in the control second group of rats injected with AdGFP vectors, though morphologically different, shows a similar stimulus/response amplitude relationship. FIG. 14 depicts the evoked response recorded at 0.5 mA of sciatic stimulation. In contrast, the same level of stimulation evoked a robust response in the experimental first group of rats injected with AdLC on the day of surgery, but failed to produce a response on day five post-surgery. While no change in stimulus response threshold is detected in the control second group of control rats injected with AdGFP, the threshold for evoked gastrocnemius EMG tripled between the day of surgery and post-surgery day 5 in the experimental first group of rats injected with AdLC.

Figure 15:
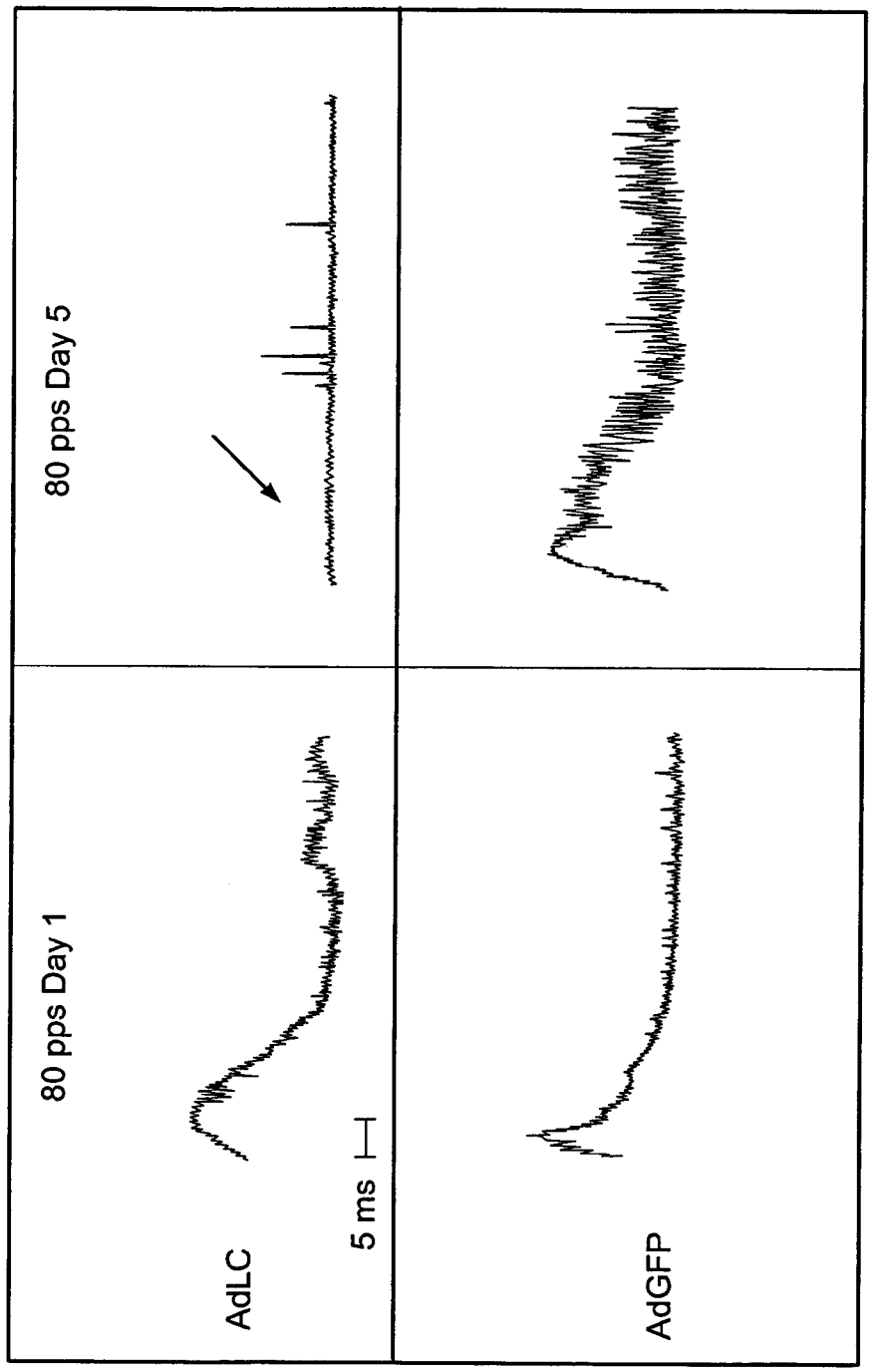
FIG. 15 depicts evoked gastrocnemius EMG results of tetanic (repeated) sciatic nerve stimulation in rats injected with a vector containing a tetanus toxin light chain peptide (AdLC) and rats injected with AdGFP on day one of injection and day five thereafter.

Furthermore, the extinction pattern for the response in the control second group of rats and the experimental first group of rats across the two test days also shows a marked difference. On day one, all rats injected with either AdLC or AdGFP have a build-up of EMG activity that peaks approximately four to five milliseconds after stimulus onset. Subsequently, the magnitude of the response diminishes, or weakens, as the synapse is overdriven. FIG. 15 demonstrates that this pattern is preserved in the control second group of rats five days post-surgery. The extinction pattern is absent in the experimental first group of rats injected with AdLC even at more than twice the initial current level. When the response appears, it is at a stimulus amplitude that is three times that required on day 0 and shows a distinctly different pattern marked by a profound delay in the response build-up. Taken together, evoked gastrocnemius EMG response to sciatic stimulation demonstrates that spinal cord LC gene expression profoundly altered synaptic transmission at the neuromuscular junction.

Example 10

Inhibition of Synaptic Transmission by LC Gene Expression is Not Due to LC Gene Induced Cytotoxicity as Evidenced by Surviving Motor Neuron Density After LC Delivery To eliminate the possibility that sensorimotor dysfunction results from LC gene induced motor neuron death, the effect of LC gene expression on surviving motor neuron density is measured in a primary E15 motor neuron (MN) culture and rat spinal cord during adenovirus gene expression.

With respect to the effect of LC gene expression on surviving motor neuron density in a primary MN culture, rat spinal cords are dissected from E15 Sprague Dawley rat embryos (Harlan, Indianapolis, Ind.) after perineural membranes are removed. The spinal cords are sectioned into 2-3 millimeter pieces and dissociated by incubating in 0.05% trypsin for 15 minutes at 37° C. followed by trituration for 3 minutes with a serum-coated glass Pasteur pipette. MNs are isolated from the cell suspension over 6.8% solution of Metrizamide in Leibowitz's L-15 media by centrifugation for 15 minutes at 1,000 gravitational force (g). 48 hours later, the cultures are exposed to 20 µl AdLC (moi of 5) (referred to as AdLC5), 50 µl AdLC (moi of 12.5) (referred to as AdLC 12.5), 50 µl AdGFP (moi of 12.5) or PBS (See Example 1 for further description of vectors). Four days later MNs are fixed in 2% PFA (Sigma-Aldrich, St. Louis, Mo.) for 10 minutes followed by 2 washes in PBS for 5 minutes each. MNs are assessed using a terminal deoxynucleotidyl transferase-mediated dUTP-digoxigenin nick end labeling (TUNEL) method. Specifically, MNs are TUNEL stained with an Apoptag Plus peroxidase kit (Serologicals, Norcross, Ga.) and counter-stained with hemotoxylin. MN density is calculated before and after adenovirus infection to further detect any possible deleterious effects of LC gene expression in MNs. MNs are visualized under a microscope (Leica, Buffalo, N.Y.) and counted in four random fields from each of four separate wells. The MN numbers and the percentage of TUNEL positive MNs for all conditions (cultures exposed to 20 µl AdLC, 50 µl AdLC12.5, 50 µl AdGFP, and PBS) are calculated and statistically analyzed.

Figure 16:
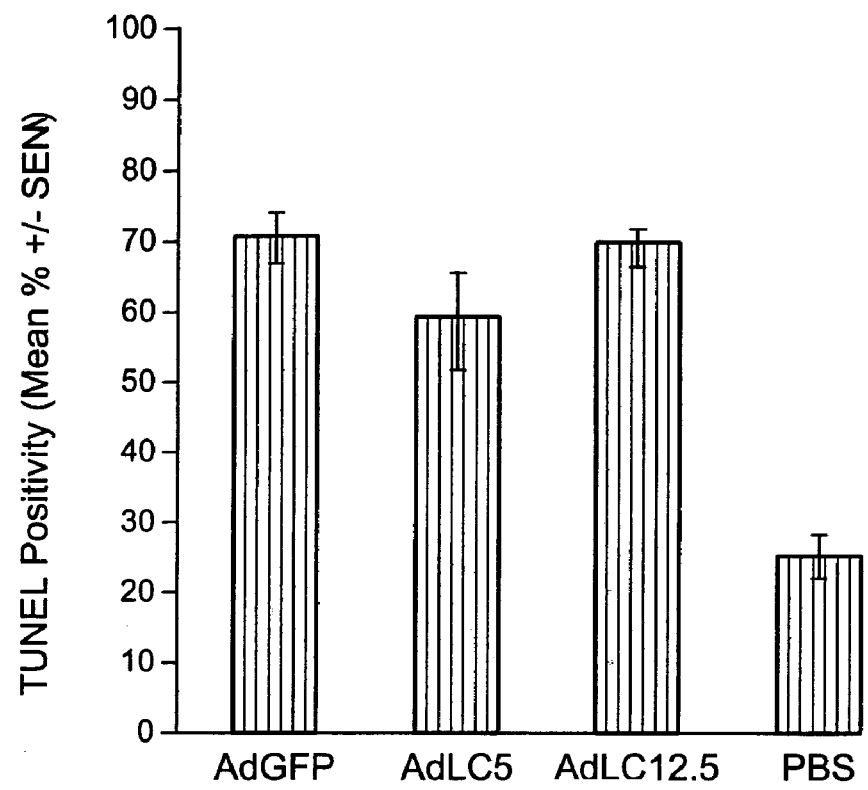
FIG. 16 is a graph of the percent of TUNEL positive cells in an E15 motor neuron culture 48 hours after being treated with PBS, a vector containing a tetanus toxin light chain peptide (AdLC5), a higher titer concentration of a vector containing a tetanus toxin light chain peptide (AdLC12.5), AdLacZ, or AdGFP.
Figure 17:
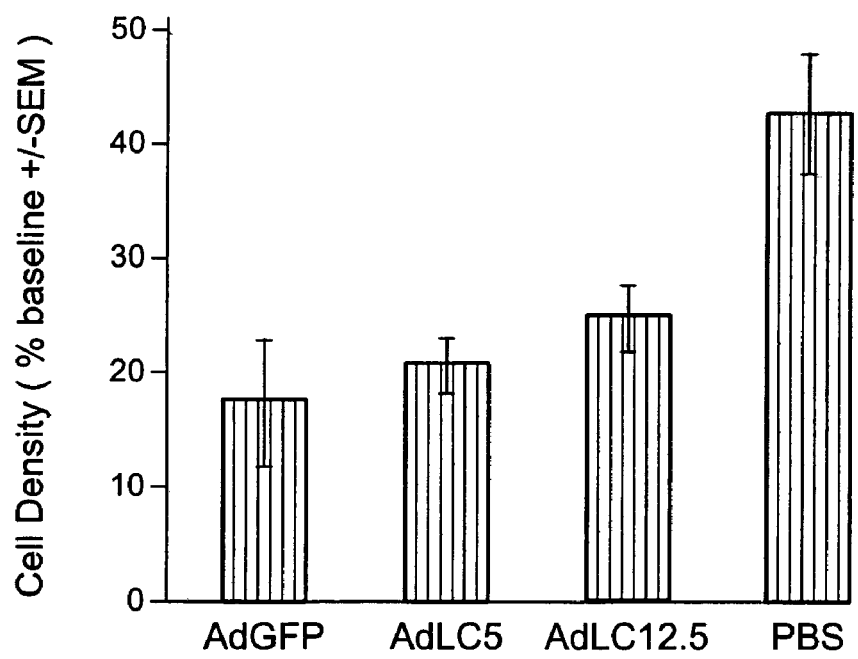
FIG. 17 is a graph of the cell density of cells from an E15 motor neuron culture 48 hours after being treated with PBS, AdLC12.5, AdLacZ, or AdGFP.

As shown in FIG. 16, there is no difference in the mean percentage of TUNEL positive MNs between AdLC treated cultures expressing both LC and GFP at different concentrations, or AdGFP treated cultures expressing GFP alone. When these virus infection groups of MNs are compared to MNs exposed to PBS, there is a statistically significant difference in the percentage of TUNEL positivity (n=12, P<0.001) reflecting a cytopathic effect of first generation adenovirus in MNs in vitro. The change in in vitro MN cell density following vector exposure also reveals a difference between PBS and adenovirus vector treated wells (n=12, P<0.001), but not between wells treated with different titers of AdLC or AdGFP (See FIG. 17). Such results indicate an adenoviral but not LC gene related reduction in cell density.

MN counts and spinal cord TUNEL staining is also analyzed after in vivo adenoviral LC gene delivery into rat spinal cord during the peak behavioral effect of LC gene expression. Lumbar spinal cords of rats sacrificed on day five post-injection as described in Example 5 are dissected, post-fixed in 2% paraformaldehyde, serially sectioned on a cryostat, and placed on slides. Prior to cover-slipping, 20 µm spinal cord sections are TUNEL stained using an Apoptag Apoptosis detection kit (Serological, Norcross, Ga.). Slides are cover-slipped with anti-fading gel for microscopic analysis. TUNEL positive cells are visualized microscopically and counted in four random fields from four separate slides for both AdLC and AdGFP conditions. These conditions are selected for comparison based on the indication that GFP may have inherent neurotoxicity. The percentage of TUNEL positive cells for each condition is calculated and statistically analyzed.

Figure 18:
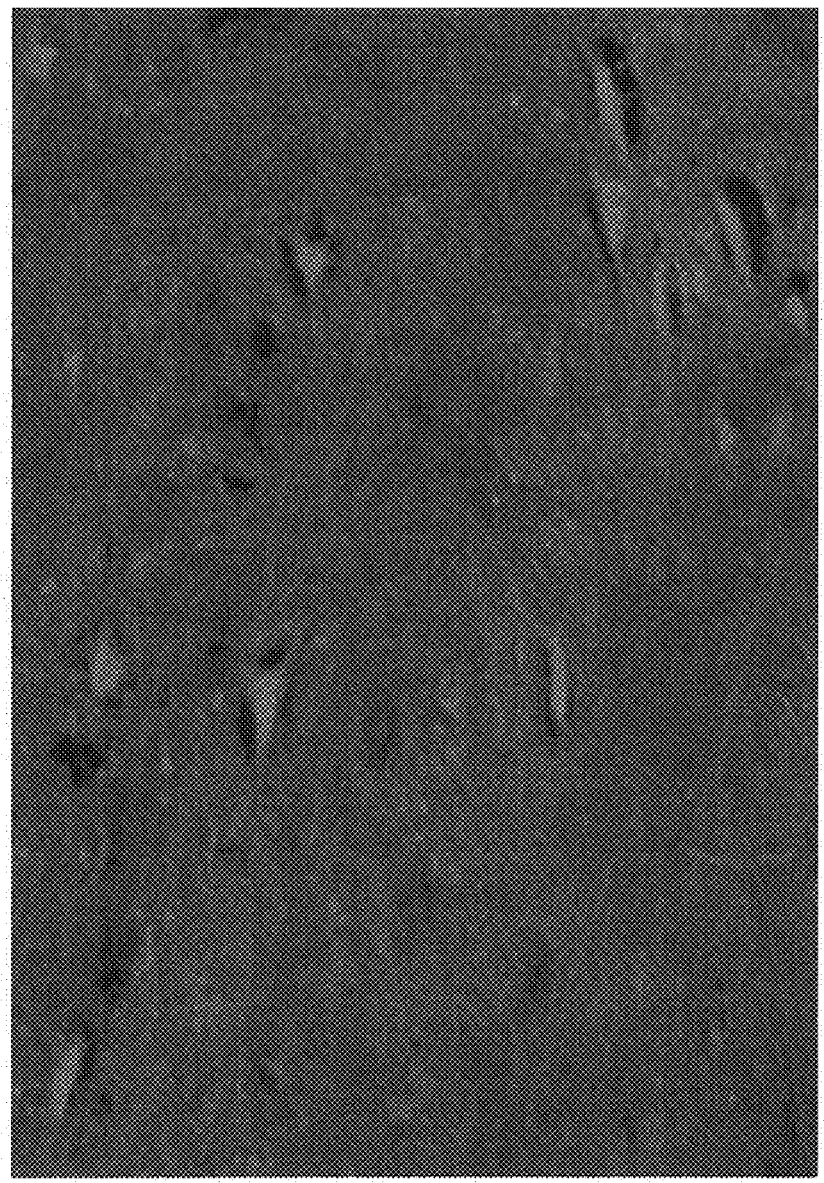
FIG. 18 is a photograph of spinal motor neurons from the injection site of a vector containing a GFP reporter gene.
Figure 19:
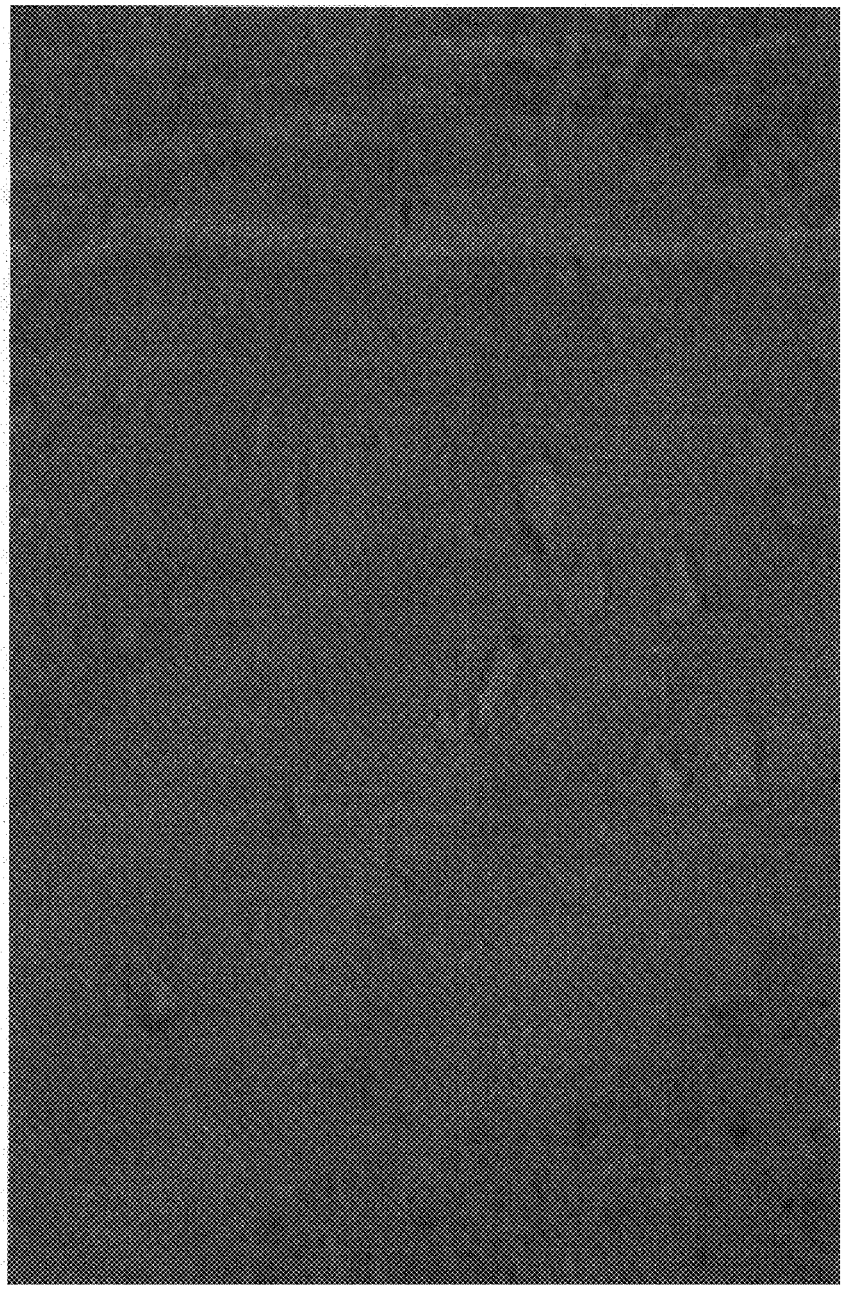
FIG. 19 is a photograph of spinal motor neurons from the injection site of a vector containing a gene encoding a tetanus toxin light chain peptide and GFP reporter gene.

Statistical comparison of the numbers of TUNEL positive MNs and MN density reveal no differences between the spinal cords of AdLC and AdGFP injected rats five days after injection. Both MN density and TUNEL staining are evaluated in the region of greatest gene expression. TUNEL staining MNs have a uniformly small size without identified axons. No positive TUNEL staining is detected in cells with motor neuron morphology. The number of TUNEL positive neurons in AdGFP injected animals is statistically indistinguishable from the number detected in AdLC injected animals (p>0.05). However, TUNEL staining only reveals neurons in the process of apoptotic death. As such, this measurement may not detect neurons that have already died. Therefore, the number of intact motor neurons are counted in the spinal cords of AdLC and AdGFP at the point of maximal sensorimotor deficit. As shown in FIGS. 18 and 19, GFP-positive motor neurons show no morphological difference between AdLC and AdGFP injected rat spinal cords. Specifically, FIG. 18 is a 40× view of spinal motor neurons from the injection site of AdGFP and reveals persistence of cells with MN morphology. FIG. 19 is 40× view of spinal MNs from the injection site of AdLC and reveals persistence of cells with MN morphology. AdLC injected animals have an average of 33 (+/−2) motor neurons per field, not significantly different from 31 (+/−6) motor neurons in the AdGFP injected rats (p>0.05).

Example 11

Inhibition of Synaptic Transmission by LC Gene Expression is Not Due to LC Gene Induced Cytotoxicity as Evidenced by Functional Recovery of Rats After LC Delivery In addition to data described in Example 10 regarding motor neuron survival during LC gene expression and sensorimotor dysfunction, functional recovery of rats after AdLC delivery is observed to confirm that observed suppression of sensorimotor function results from synaptic transmission suppression rather than motor neuron death.

To demonstrate recovery, rats undergo unilateral spinal cord injection with either 5 µl of AdLC (titer 7.8×10$^9$ PFU/ml, n=4) or 5 µl of AdGFP (titer 7.8×10$^9$ PFU/ml, n=4) according to the bilateral injection protocol described in Example 4.

The behavior of the rats is tracked for one month after surgery. The rats are tested weekly on the BBB scale as previously described, starting in the first pre-operative week, for a total of 5 weeks. In addition, muscle strength of each hindlimb is measured using an automated Grip Strength Meter (Columbus Instruments, Columbus. Ohio). The Grip Strength Meter provides a validated measurement of motor function. The instrument uses an electronic digital force gauge that measures the peak force exerted upon it by the action of an animal. For the hindlimb grip strength measurement, each rat is first held with its back facing the sensor. The forepaws are supported and each rat is allowed to place each individual hindpaw on the angled wire mesh of a pull bar. These handling maneuvers allow each rat to grasp the pull bar with the hindpaw. Each rat is slowly pushed towards the pull bar at a rate of 2-3 centimeters/second until it is releases the pull bar. Peak compression is recorded from the force gauge's digital readout. Each rat is tested in five sequential trials and the highest value is considered. Motor function assessment in each hindlimb is assessed weekly, starting pre-surgery, for a total of five weeks. The presurgery values of both limbs are averaged in each rat and considered the baseline for that rat. Grip strength motor function in the injected and non-injected sides is expressed as a percent baseline. The motor deficit is calculated as the difference between hindlimb values in the injected and non-injected sides.

Prior to surgery, all rats have a BBB score of 21. Postsurgery, following a two hour recovery, all rats are ambulating using all four limbs with an approximate BBB score of 21. The BBB score in the AdLC injected rats decreases to 10 on post-surgery day five, reflecting a unilateral motor deficit in the injected side hindlimb. Rats injected with AdGFP fully maintain their locomotor abilities (BBB=21). On day 10-11, rats injected with AdLC start improving with their BBB score increasing to 14.3 which still reflects significant motor deficit. However, the average BBB score of rats injected with AdLC on day 20 post-surgery reaches 18.3 expressing overall good motor function with minor balance deficit and some decrease in consistency of paw positioning. One month post-surgery the average BBB in the rats injected with AdLC remains stable at 19, demonstrating significant recovery of function as compared to day 5 post-surgery (p<0.05). Rats injected with AdGFP maintain BBB above 20, with one rat injected with AdGFP have a BBB score below 20 approximately three weeks post-surgery. This change, which reflects some loss of balance and tail positioning, maybe due to the delayed gliosis and myelomalacia that has previously been noted in spinal cords injected with adenovirus.

Figure 20:
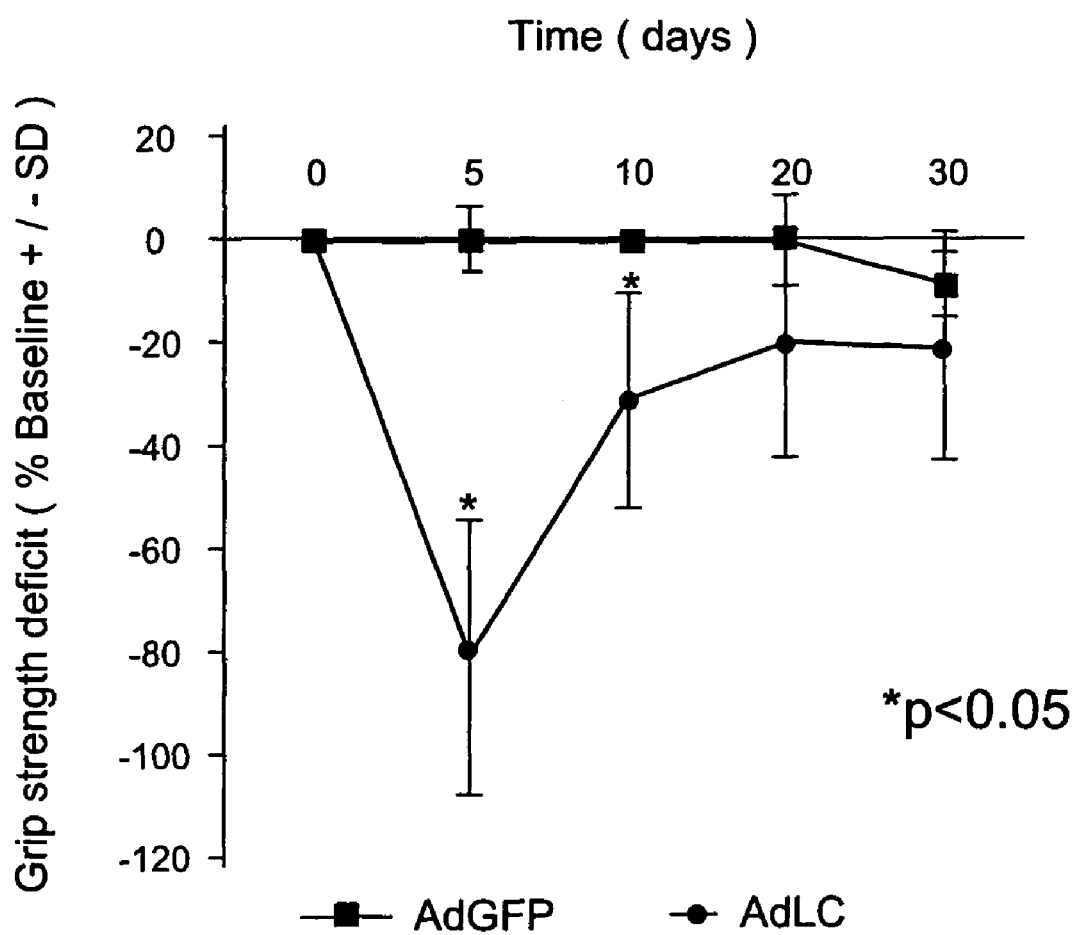
FIG. 20 is a chart depicting the grip strength deficit of rats injected with AdLC or AdGFP over a 30 day period.

In the week prior to surgery, the average unilateral hindlimb grip strength is 254 grams in rats injected with AdLC and 231 grams in rats injected with AdGFP. The hindlimb right-sided grip strength deficit derived by comparing treated and untreated sides is plotted normalized to the preoperative baseline. FIG. 20 illustrates that rats injected with AdLC show a peak motor deficit at day 5 with significant recovery by one month post injection (p<0.05). Specifically, AdLC-induced deficit in unilateral grip strength is −80% of baseline values on day 5, significantly different from that of rats injected with AdGFP, which had no detectable deficit (0.15% baseline). Ten days post-surgery, the grip strength deficit in rats injected with AdLC is reduced to −31% of baseline, still significantly (p<0.05) different from rats injected with AdGFP (−0.66%) and decreased further to −19% on days 20 and stabilized to −20% around 30 days post-surgery, statistically not significant (P=0.16). The rats injected with AdGFP demonstrate a slight decrease in grip strength at 30 days post-surgery (−8%) due to a minimal decrease in function in one rat, which did not reach statistical significance. Thus, both BBB assessments and unilateral hindlimb grip strength measurements depict a functional deficit in rats injected with AdLC and a subsequent improvement in such functional deficit after time, indicating that the functional deficit is due to LC gene expression and not MN death.

Statistical Analysis

TUNEL positive primary motor neurons and the rat spinal cord, primary motor neuron cell density and rat behavioral data (BBB scores and Vmax) are analyzed with Origin 7.0 Software. The percentage of TUNEL positive motor neurons and cell density in E15 culture for each treatment condition are compared using a one-way analysis of variance (ANOVA) with multiple comparison procedures (Tukey Test) (n=4 for each group). A similar analysis is performed on the mean density of TUNEL positive cells per section from animals treated with AdLC and AdGFP vectors (Example 10).

Analysis of behavioral data utilizes an intensive, within-subjects design. A BBB score is assigned to each subject daily and the mean (+/−SEM) values for each treatment group is determined. Each animal is tested on the rotarod and the Vmax is calculated and expressed as a percentage of the pre-surgery baseline value. A value identical to the pre-surgery baseline is therefore equal to 100%. Repeated measures analysis of variance (ANOVA) is performed. One-way ANOVA and Tukey-Kramer post-hoc multiple comparison statistics compares the motor function parameter (either BBB scores or Vmax) following AdLC, AdGFP, AdLacZ and AdLC/10 injections at each time point. Time points include pre-surgery (Day-1) and five days postsurgery (Day 1-5). Probability values of P<0.05 are regarded as statistically significant. Behavioral data from the long-term cohort is analyzed using Student t-test to compare AdLC and AdGFP groups at each time point. ANOVA is used to assess changes in motor function in the two groups across five time-points.

Example 12

Administration of LC Gene In Vivo Improves Spasticity in a Spastic Mouse Model as Evidenced by Behavioral and Anatomical Assays The spastic mouse demonstrates the development of spastic tone and muscle/tendon contractures as the result of a mutation in the glycine receptor, which reduces the general inhibitory tone in the animal's nervous system. The application of botulin neurotoxin to these animals has been documented to reduce contracture that develops in these animals secondary to spasticity throughout development. This model provides an approximation of human cerebral palsy.

Spastic phenotype mice are selected from litters and paired with two non-spastic litter mates on day 20 of life. Mice are injected in the left sciatic nerve with $2\lambda$ of the maximal titer of AdLC or AdGFP (n=20 per group) (See Example 1). Mice are evaluated for spasticity using a modified Ashworth Scale in the right and left leg by a blinded scorer as well as incline plane measurements on a weekly basis. Animals are sacrificed on day 65 of life to undergo gastrocnemius to tibial ratio measurement. This anatomical measurement quantifies the degree of chronic spasticity in each animal.

B6C3Fe-a/a-Glrbspa/+breeding pairs of spastic mice are purchased and bred. Litters are examined beginning at 14 days for homozygous spastic phenotype mice. The spasms consist of rapid tremor, stiffness of posture, and difficulty in righting when placed on the back. Litter mates are selected as controls.

Mice are placed headfirst into a 30 cc syringe fitted into a 60 cc syringe attached to the open circuit gas anesthesia system. Isofluorane is administered as described in Example 4.

Viral vectors AdLC and AdGFP are placed in phosphate buffered saline (PBS) with 20% sucrose used as a cryoprotectant. Nerves of the spastic mice are injected with an oocyte microinjector (Drummond: nanoject, Broomall, Pa.). A glass micropipette puller (Narishige: PP-83, Tokyo, Japan) is used to create tapered tips on micropipettes which are then beveled to a 100 μm diameter tip under microscopic visualization. Glass micropipettes are placed on the oocyte injector which is advanced through the perineurium along the axis of the nerve with the use of a micromanipulator (Narishige: N-152, Tokyo, Japan), while gentle counter traction is applied to the nerve. $0.5\lambda$ are delivered in a series of ten 50 nl boluses, injected at four separate puncture sites for a total of $2\lambda$.

Using a modified Ashworth scale, an individual blinded to the treatment category scores the degree of spasticity at the hip, knee, and angle on a 0-5 scale as follows for the right and left limb score:

0=No increase in tone during flexion and extension

1=Catch and release or minimal resistance

2=Catch with minimal resistance

3=Increased tone throughout motion, easy movement

4=Considerably increased tone, difficult movement

5=Rigidity on flexion or extension

The degree of gastrocnemius contractures is estimated in the spastic mouse model by measuring the length of the gastrocnemius and tibia and tabulating the ratio of these values for both hindlimbs.

AdLC results in reduced spasticity and contractures. Further, the injected limb shows disproportionate improvement in spasticity in comparison with the right limb.

Example 13

Administration of LC gene In Vivo Improves Spinal Cord Contusion Induced Spasticity as Evidenced by Behavioral Assays Human spinal cord injury is rarely the result of focused lesions or transaction. More commonly spinal cord injury results from cord crush or contusion. This trauma is one of the leading causes of spasticity. A range of spinal cord contusion severities can be induced with a weight drop model. The study of a larger rodent model allows for more sensitive assays of spasticity to be applied including electrophysiology and the measurement of dynamic limb resistance. Such assays allow for better resolution of the dose response defining titers of virus that can reduce spasticity without exacerbating weakness.

Groups of Sprague-Dawley rats undergo simultaneous left sciatic nerve vector administration and thoracic spinal cord injury. Specifically, rats in each treatment group (AdLC or AdGFP (See Example 4) (n=15/group) undergo a 5 centimeter (cm) weight drop injury (see below) and injection of 3 separate titers of virus vector $10^4$, $10^6$, $10^8$, pt/μl. Dynamic force amplitude (DFA) and incline plane assays are measured biweekly for four weeks following injury. At the end of four weeks, animals undergo measurement of bilateral monosynaptic reflex potentials (MSR) from the sciatic nerves. The ratio of MSR and dynamic force amplitudes in treated to untreated limbs is calculated. These ratios are compared between groups as well as to the raw values of MSR and DFA.

To impart spinal cord injury on the rats, based on the New York University weight-drop device, a spinal cord impounder is designed to deliver reproducible contusions to the spinal cord. The midthoracic spinal cord is exposed as described above in Example 4. During the operation, the spinal cord impounder is positioned over the cord at the laminectomy defect. The spine is immobilized with modified Alice clamps fixed to the spinous processes rostral and caudal to the laminectomy. A 10 gram weight is dropped a standard distance along a track and strikes a Teflon impounder tip that contuses the cord. The force transduced into the spinal cord is measured with a tension transducer to insure consistent injury. Spinal cord injury results in partial or complete paralysis.

To perform a DFA assay, a modification dynamic force amplitude apparatus is constructed. Specifically, this apparatus utilizes an electric motor that rotates a first wheel, which is attached via a rod to a second wheel. This construction results in oscillation of the wheel similar to the principle that converts piston movement to rotary motion in locomotive wheels. The second wheel is connected to a fulcrum that is in turn attached to "boots." As the second wheel oscillates, the rat's foot is dorsiflexed rhythmically at the ankle. Tension transducers are placed under footpads of the boots to detect the resistance to dorsiflexion. The means resistance to flexion over a series of trials is calculated. In addition, the rate of dorsiflexion is altered to look at the resistance/rate ratio.

Administration of AdLC but not AdGFP reduces DFA. Antispasticity effects are greater in the in the treated limb than the contralateral side, but a degree of improvement in the contralateral limb is seen as well, since some gene expression is seen in the contralateral motor neurons.

Example 14

Administration of LC gene In Vivo Reduces Parkinsonian Symptoms in a Parkinsonian Monkey as Evidenced by Behavioral Assays To determine the effect of AdLC administration on Parkinsonian symptoms in a mammal, a MPTP Parkinson animal model is utilized. Two rhesus monkeys (*Macaca mulatta*) are utilized. Both monkeys are treated with MPTP via a single injection through the internal carotid artery (left side in the first, right side in the second). The total amounts of MPTP is 0.6 mg/kg. Both monkeys develop a stable Parkinsonian state characterized by contralateral rigidity and bradykinesia as is consistently observed in this animal model of Parkinsonism.

Monkeys are anesthetized with isoflurane (3% in $O_2$) and placed in a Kopf stereotaxic frame (David Kopf Instruments, Tujunga, Calif.) and 4 microliters of AAVCMVLC-IRESGFP ($1\times10^9$ PFU/ml: See Example 2) is injected into the left subthalamic nucleus (STN) of one monkey and 4 microliters of AAVGFP ($1\times10^9$ PFU/ml: See Example 2) is injected into the left STN of the other monkey. AAV mediated LC gene expression is employed in this experiment to achieve more durable LC gene expression. Four to five months after surgery, expression of the LC gene and GFP reporter gene is determined by immunofluorescence. Robust expression confined to the STN is obtained for the LC gene and GFP reporter gene.

Behavior is assessed by measuring the amount of spontaneous movement using a computer-assisted method of behavioral assessment to quantify the amount of movement ("Reversal of experimental Parkinsonism by lesions of the subthalamic nucleus," Science 249: 1436-1438 (1990), which is incorporated by reference herein). Each session is videotaped for subsequent rating by examiners blinded to the experimental condition. During the videotape ratings two scorers (blinded to the experimental condition) count the movement time per 10 minutes for the arm and leg on the right and left sides of the body from the video. A post hoc analysis (Tukey's honestly significant difference) is used to determine the significance of the difference in amount of time of limb movement. Muscle tone of the biceps brachii muscles evoked by manual elbow extension contralateral to the injection site is assessed using EMG.

The monkey injected with AAVCMVLC-IRESGFP shows increased spontaneous movement and decreased rigidity and bradykinesia. In contrast, the monkey injected with AAVGFP sits quietly with little movement of the extremities (bradykinesia). The administration of AAVCMVLC-IRESGFP also reduces bicep brachii EMGs induced by manual elbow extension.

Example 15

Administration of LC Gene In Vivo Reduces Epileptic Seizures in Epileptic Rats

Adult male Sprague-Dawley rats weighing 350-400 grams are anesthetized with halothane and then placed on a heating pad in a stereotaxic frame (David Kopf Instruments, Tujunga, Calif.) that allows continuous halothane administration through a nosepiece. A craniotomy is performed while the rats are breathing 4% halothane, which is reduced to <1% when seizures are induced. After infiltrating the skin with 2% lidocaine, a 5×10 mm cranial window over the anterior left hemisphere is created using a dental drill. The window is extended medially to the sagittal sinus and 5 mm anterior and posterior to the coronal suture. After creation of the window, the dura is gently opened to allow drug injection. 0.5 µl of a 4-AP solution (25 mM in artificial CSF using a commercial oocyte injection system (Drummond Scientific, Broomall, Pa.) coupled to a glass micropipette (tip diameter about 100 µm)) is injected into the motor cortex of the rats. Specifically, the injection system is mounted on a micromanipulator that allows administration of the 4-AP 0.5 mm below the surface of the motor cortex, at a position 2 mm anterior to the bregma and 2.5 mm from the midline. The actual injection is carried out over 5 minutes to minimize cortical trauma, and the pipette is left in place for 20 minutes to minimize leakage of the 4-AP.

Two screw electrodes are placed symmetrically over each hemisphere and differentially record the electroencephalogram (EEG) between the two electrodes using standard amplifiers. The EEGs are digitized and archived using standard hardware and software. EEG monitoring is performed prior to injection of the 4-AP and is continued throughout the entire experiment. Seizure onset is readily recognizable as an abrupt increase in EEG frequency and amplitude.

5 microliters of AdLC ($1\times10^9$ pfu/ml: See Example 1) in injected into the motor cortex of one group of rats and 5 microliters of AdGFP (See Example 1) is injected into the motor cortex of another group of rats.

No seizures are detected in rats after craniotomy. Within 30 minutes of 4-AP injection, rats injected with AdGFP and control rats (injected with neither AdLC or AdGFP) develop recurrent clinical (paw twitch) and electrographic seizures that remain for two hours. The seizure duration is 85.7±26.2 seconds. Rats injected with AdLC have reduced seizure duration and seizure frequency compared to rats injected with AdGFP and control rats indicating that administration of AdLC reduces epileptic seizures.

Methods involving conventional molecular biology techniques are described herein. Such techniques are generally known in the art and are described in detail in methodology treatises, such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., *J. Am. Chem. Soc.* 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

The foregoing description and examples have been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

I claim:

1. A method of producing a *clostridial* neurotoxin light chain peptide in cells transplanted into a target site of a body, the method comprising:

transfecting cells in vitro with a nucleic acid construct comprising (a) a nucleic acid encoding a *clostridial* neurotoxin light chain peptide and (b) a regulatory sequence operably linked to the nucleic acid to allow expression of the nucleic acid in the transfected cells, selecting the transfected cells that express the nucleic acid and thereby produce the *clostridial* neurotoxin light chain peptide; and transplanting into a target site of a body the selected transfected cells that produce a *clostridial* neurotoxin light chain peptide.

2. The method of claim 1, wherein the cells are neurons.

3. The method of claim 1, wherein the target site is the spinal cord.

* * * * *